(12) United States Patent
Lee

(10) Patent No.: US 7,364,582 B2
(45) Date of Patent: *Apr. 29, 2008

(54) SURGICAL INSTRUMENT

(75) Inventor: Woojin Lee, Hopkinton, MA (US)

(73) Assignee: Cambridge Endoscopic Devices, Inc., Framingham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/429,796

(22) Filed: May 8, 2006

(65) Prior Publication Data

US 2006/0206101 A1    Sep. 14, 2006

Related U.S. Application Data

(63) Continuation of application No. 10/822,081, filed on Apr. 12, 2004, now Pat. No. 7,147,650.

(60) Provisional application No. 60/515,560, filed on Oct. 30, 2003.

(51) Int. Cl.
*A61B 17/28* (2006.01)

(52) U.S. Cl. .................. 606/205; 606/167

(58) Field of Classification Search .......... None
See application file for complete search history.

(56) References Cited

U.S. PATENT DOCUMENTS

| 2,028,635 | A | 1/1936 | Wappler |
| 2,507,710 | A | 5/1950 | Grosso |
| 2,790,437 | A | 4/1957 | Moore |
| 3,557,780 | A | 1/1971 | Sato |
| 3,858,577 | A | 1/1975 | Bass et al. |
| 3,895,636 | A | 7/1975 | Schmidt |
| 4,483,562 | A | 11/1984 | Schoolman |

(Continued)

FOREIGN PATENT DOCUMENTS

EP    0 095 970 A2    12/1983

(Continued)

OTHER PUBLICATIONS

Hiromasa Yamashita et al., "Multi-Slider Linkage Mechanism for Endoscopic Forceps Manipulator," In Proc. of the 2003 IEEE/RSJ, Intl. Conference on Intelligent Robots and Systems, vol. 3, pp. 2577-2582, Las Vegas, Nevada, Oct. 2003.

(Continued)

*Primary Examiner*—Glenn K. Dawson
(74) *Attorney, Agent, or Firm*—David M. Driscoll, Esq.

(57) ABSTRACT

An endoscopic or laparoscopic instrument includes a distal tool, a rigid or flexible elongated shaft that supports the distal tool, and a proximal handle or control member, where the tool and the handle are coupled to the respective distal and proximal ends of the elongated shaft via bendable motion members. The tool and the tool motion member are coupled to the handle and the handle motion member via cables and a push rod in such a way that the movement of the handle with respect to the elongated shaft in any direction is replicated by the tool at the distal end of the shaft. The magnitude of the tool motion with respect to the handle motion may be scaled depending on the size of the handle motion member with respect to that of the tool motion member.

63 Claims, 40 Drawing Sheets

U.S. PATENT DOCUMENTS

| | | | |
|---|---|---|---|
| 4,688,554 A | 8/1987 | Habib | |
| 4,728,020 A | 3/1988 | Green et al. | |
| 4,763,669 A | 8/1988 | Jaeger | |
| 4,872,456 A | 10/1989 | Hasson | |
| 4,880,015 A | 11/1989 | Nierman | |
| 4,944,093 A | 7/1990 | Falk | |
| 4,944,741 A | 7/1990 | Hasson | |
| 4,945,920 A | 8/1990 | Clossick | |
| 5,002,543 A | 3/1991 | Bradshaw et al. | |
| 5,042,707 A | 8/1991 | Taheri | |
| 5,209,747 A | 5/1993 | Knoepfler | |
| 5,271,381 A | 12/1993 | Ailinger et al. | |
| 5,273,026 A | 12/1993 | Wilk | |
| 5,275,608 A * | 1/1994 | Forman et al. | 606/170 |
| 5,314,424 A | 5/1994 | Nicholas | |
| 5,330,502 A | 7/1994 | Hassler et al. | |
| 5,344,428 A | 9/1994 | Griffiths | |
| 5,383,880 A | 1/1995 | Hooven | |
| 5,386,818 A | 2/1995 | Schneebaum et al. | |
| 5,395,367 A | 3/1995 | Wilk | |
| 5,405,344 A * | 4/1995 | Williamson et al. | 606/1 |
| 5,433,721 A | 7/1995 | Hooven et al. | |
| 5,441,494 A | 8/1995 | Ortiz | |
| 5,454,827 A | 10/1995 | Aust et al. | |
| 5,501,654 A | 3/1996 | Failla et al. | |
| 5,511,564 A * | 4/1996 | Wilk | 128/898 |
| 5,520,678 A * | 5/1996 | Heckele et al. | 606/1 |
| 5,618,294 A | 4/1997 | Aust et al. | |
| 5,643,294 A * | 7/1997 | Tovey et al. | 606/148 |
| 5,702,408 A * | 12/1997 | Wales et al. | 606/139 |
| 5,759,151 A | 6/1998 | Sturges | |
| 5,766,196 A | 6/1998 | Griffiths | |
| 5,772,578 A | 6/1998 | Heimberger et al. | |
| 5,823,066 A | 10/1998 | Huitema et al. | |
| 5,827,177 A | 10/1998 | Oneda et al. | |
| 5,851,208 A | 12/1998 | Trott | |
| 5,855,569 A | 1/1999 | Komi | |
| 5,873,817 A | 2/1999 | Kokish et al. | |
| 5,899,914 A | 5/1999 | Zirps et al. | |
| 5,904,647 A | 5/1999 | Ouchi | |
| 5,916,146 A | 6/1999 | Allotta et al. | |
| 5,916,147 A | 6/1999 | Boury | |
| 5,921,956 A | 7/1999 | Grinberg et al. | |
| 5,938,678 A | 8/1999 | Zirps et al. | |
| 5,944,713 A | 8/1999 | Schuman | |
| 6,126,633 A | 10/2000 | Kaji et al. | |
| 6,174,280 B1 | 1/2001 | Oneda et al. | |
| 6,210,377 B1 | 4/2001 | Ouchi | |
| 6,210,378 B1 | 4/2001 | Ouchi | |
| 6,270,453 B1 | 8/2001 | Sakai | |
| 6,551,238 B2 | 4/2003 | Staud | |
| 6,623,424 B2 | 9/2003 | Hayakawa et al. | |
| 6,638,214 B2 | 10/2003 | Akiba | |
| 6,752,756 B2 | 6/2004 | Lunsford et al. | |
| 6,761,717 B2 | 7/2004 | Bales et al. | |
| 7,147,650 B2 | 12/2006 | Lee | |
| 2002/0045803 A1 | 4/2002 | Abe et al. | |
| 2002/0095175 A1 | 7/2002 | Brock et al. | |
| 2002/0133173 A1 | 9/2002 | Brock et al. | |
| 2002/0156497 A1 | 10/2002 | Nagase | |
| 2002/0177750 A1 | 11/2002 | Pilvisto | |
| 2002/0177847 A1 | 11/2002 | Long | |
| 2003/0045900 A1 * | 3/2003 | Hahnen et al. | 606/205 |
| 2003/0065359 A1 | 4/2003 | Weller et al. | |
| 2003/0109898 A1 | 6/2003 | Schwarz et al. | |
| 2003/0135204 A1 | 7/2003 | Lee et al. | |
| 2003/0216618 A1 | 11/2003 | Arai | |
| 2004/0049206 A1 | 3/2004 | Lee et al. | |
| 2004/0111009 A1 | 6/2004 | Adams et al. | |
| 2004/0138529 A1 | 7/2004 | Wiltshire et al. | |
| 2004/0176751 A1 | 9/2004 | Weitzner et al. | |
| 2004/0193146 A1 | 9/2004 | Lee et al. | |
| 2004/0236316 A1 * | 11/2004 | Danitz et al. | 606/1 |
| 2005/0049580 A1 | 3/2005 | Brock et al. | |
| 2005/0107667 A1 | 5/2005 | Danitz et al. | |
| 2005/0228440 A1 | 10/2005 | Brock et al. | |
| 2005/0251112 A1 * | 11/2005 | Danitz et al. | 606/1 |
| 2005/0273084 A1 | 12/2005 | Hinman et al. | |
| 2005/0273085 A1 | 12/2005 | Hinman et al. | |

FOREIGN PATENT DOCUMENTS

| | | |
|---|---|---|
| EP | 0 448 284 A2 | 9/1991 |
| EP | 0 626 604 A2 | 5/1994 |
| EP | 0 427 949 B1 | 6/1994 |
| GB | 2 143 920 | 2/1985 |
| WO | WO 90/05491 | 5/1990 |
| WO | WO 92/01414 | 2/1992 |
| WO | WO 94/17965 | 8/1994 |

OTHER PUBLICATIONS

Multi-DOF Forceps Manipulator System for Laparoscopic Surgery—Mechanism miniaturized & Evaluation of New interfaces—Nakamura et al.

Multi-DOF Forceps Manipulator System for Laparoscopic Surgery—Nakamura et al.

Development of forceps manipulator system for laparoscopic surgery—Nakamura et al.

* cited by examiner

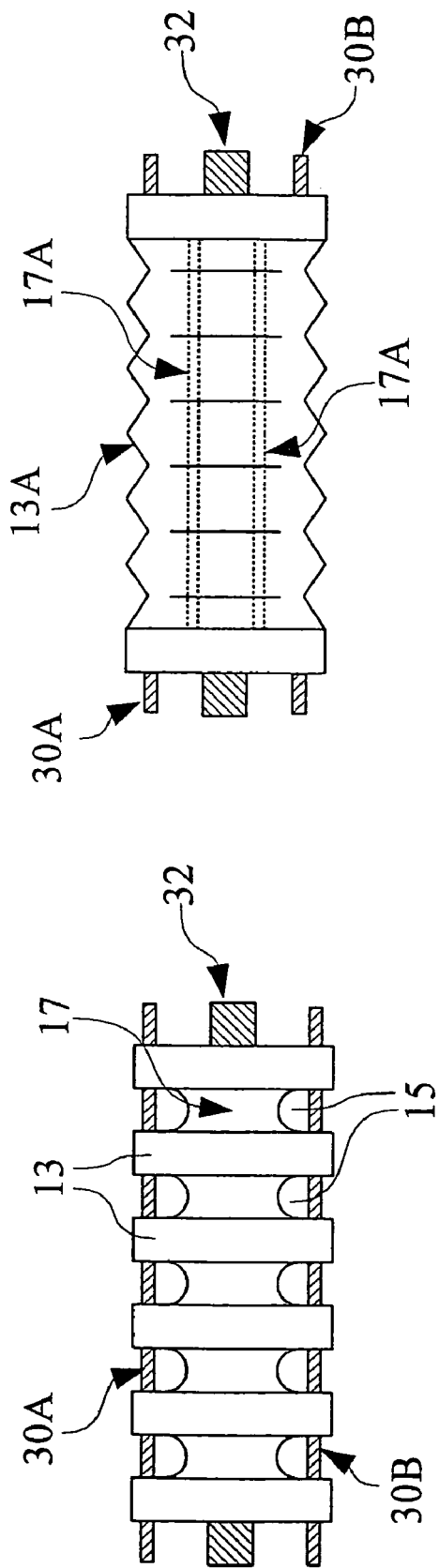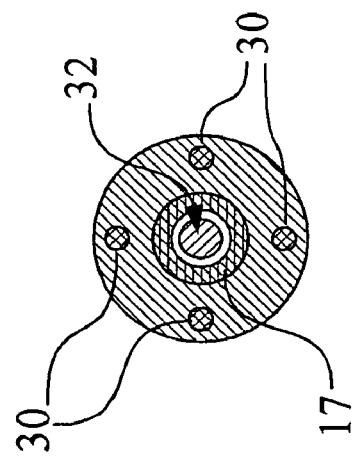
Figure 5B
Figure 5A
Figure 5C

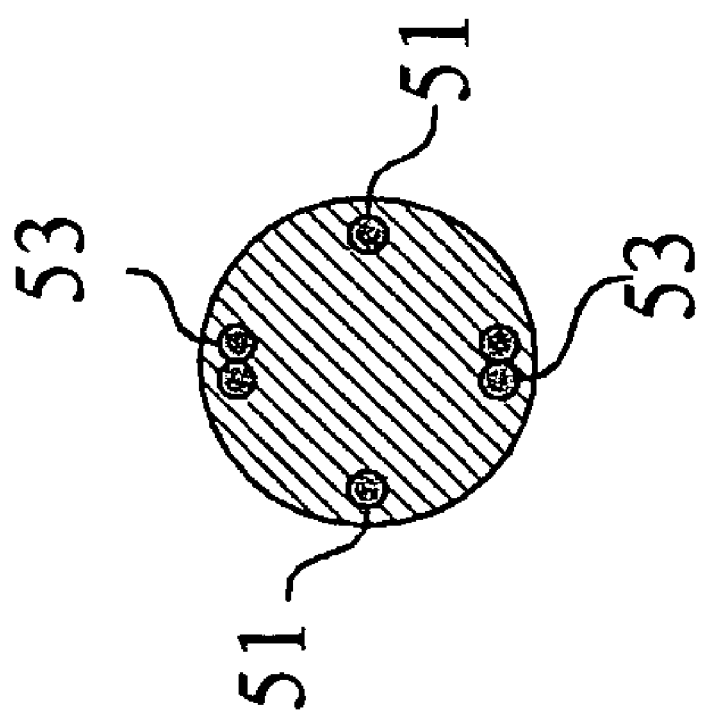

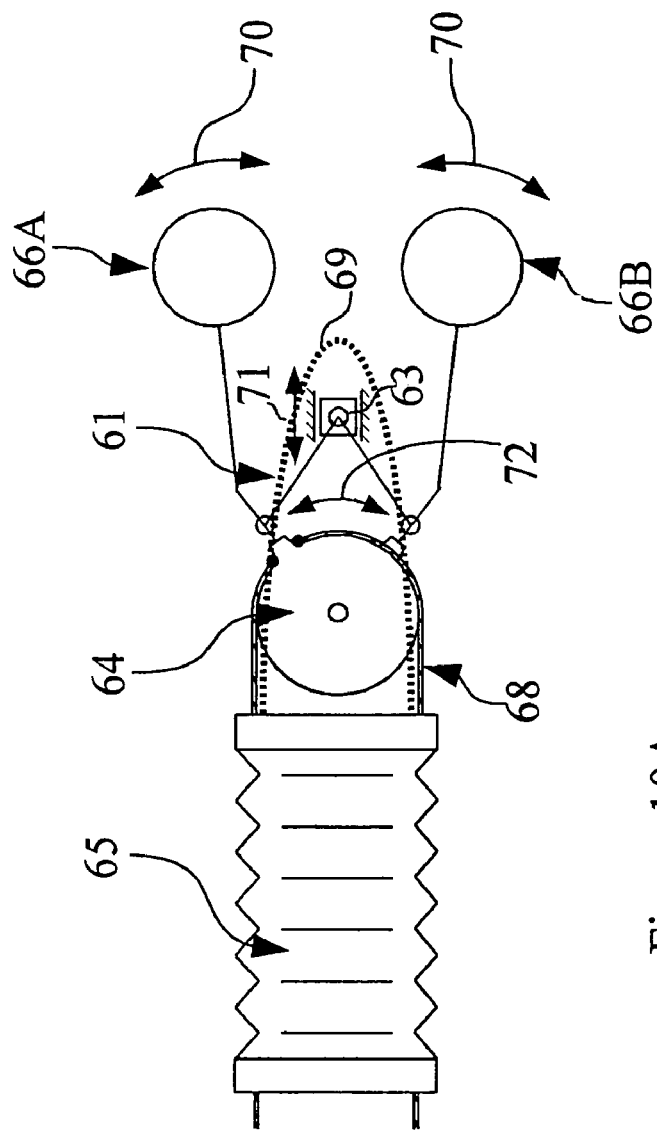
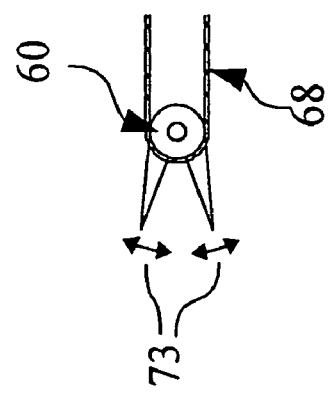
Figure 10A

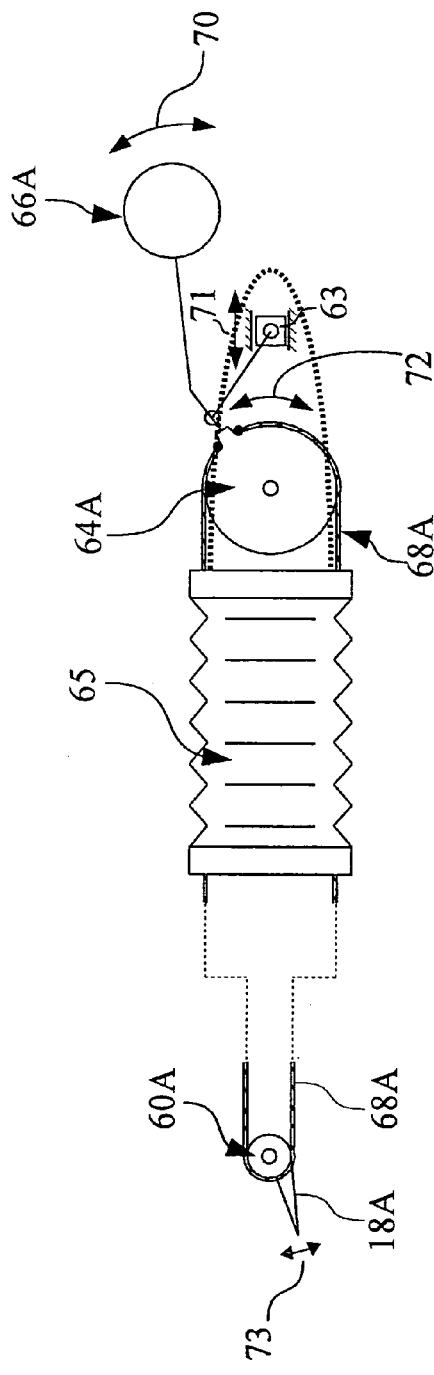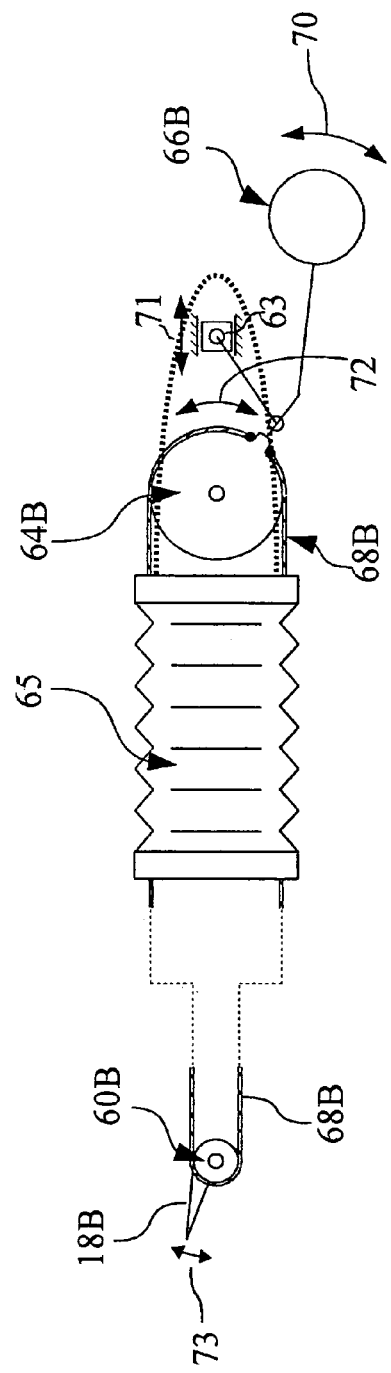

SURGICAL INSTRUMENT

RRLATED APPLICATION

This application is a continuation of U.S. patent application Ser. No. 10/822,081 filed on Apr. 12, 2004, now U.S. Pat. No. 7,147,650, which claims priority under 35 U.S.C § 119(e) to U.S. Provisional Patent Application No. 60/515,560 which was filed on Oct. 30, 2003. The content of all of the aforementioned applications is hereby incorporated by reference herein in its entirety.

BACKGROUND OF THE INVENTION

The present invention relates in general to surgical instruments, and more particularly to manually operated surgical instruments that are intended for use in minimally invasive surgery.

Endoscopic and laparoscopic instruments currently available in the market are extremely difficult to learn to operate and use, mainly due to a lack of dexterity in their use. For instance, when using a typical laparoscopic instrument during surgery, the orientation of the tool of the instrument is solely dictated by the locations of the target and the incision, which is often referred to as the fulcrum effect. As a result, common tasks such as suturing, knotting and fine dissection have become challenging to master. Various laparoscopic instruments have been developed over the years to overcome this deficiency, usually by providing an extra articulation often controlled by a separately disposed knob. However, even with these modifications these instruments still do not provide enough dexterity to allow the surgeon to perform common tasks such as suturing at any arbitrarily selected orientation.

Accordingly, an object of the present invention is to provide a laparoscopic or endoscopic surgical instrument that allows the surgeon to manipulate the tool end of the surgical instrument with greater dexterity.

SUMMARY OF THE INVENTION

In accordance with one aspect of the present invention there is provided an endoscopic or laparoscopic instrument that is comprised of a distal tool, a rigid or flexible elongated shaft that supports the distal tool, and a proximal handle or control member, where the tool and the handle are coupled to the respective distal and proximal ends of the elongated shaft via pivoted or bendable motion members. The tool and the tool motion member are coupled to the handle and the handle motion member via cables and a push rod in such a way that the movement of the handle with respect to the elongated shaft in any direction are replicated by the tool at the distal end of the shaft. The magnitude of the tool motion with respect to the handle motion may be scaled depending on the size of the handle motion member with respect to that of the tool motion member.

In the present invention one embodiment of the tool motion member is a bending section that is bendable in any arbitrary angle thereby providing two degrees of freedom, whereas in another embodiment, the tool motion member is comprised of the combination of a single plane bendable section and a pivotal joint. In still another embodiment, the motion member is comprised of two pivotal joints orientated orthogonal to each other. In addition to these embodiments where the motion member provides two degrees of freedom, in a situation where less dexterity is needed, the motion member can only be a one degree of freedom member, either pivotal or bendable.

In accordance with another aspect of the invention there is provided a manually operated surgical instrument primarily adapted for use in minimally invasive surgery. The instrument comprises an elongated instrument shaft having proximal and distal ends; a proximal turnable member; a control handle coupled to the proximal end of the elongated instrument shaft via the proximal turnable member; a distal turnable member; a surgical tool coupled to the distal end of the elongated instrument shaft via the distal turnable member; and a transmission element that intercouples between the proximal and distal turnable members so that a deflection of the control handle at the proximal turnable member causes a deflection of surgical tool via the distal turnable member.

In accordance with still another aspect of the invention there is provided a manually operated surgical instrument primarily adapted for use in minimally invasive surgery. The instrument comprises an elongated instrument shaft having proximal and distal ends; a tool disposed from the distal end of the instrument shaft; and a control handle disposed from the proximal end of the instrument shaft. The tool is coupled to the distal end of the elongated instrument shaft via a first movable member. The control handle is coupled to the proximal end of the elongated instrument shaft via a second movable member. The movement of the control handle with respect to the elongated instrument shaft via the second movable member causes attendant movement of the tool with respect to the elongated instrument shaft via the first movable member.

BRIEF DESCRIPTION OF THE DRAWINGS

Numerous other objects, features and advantageous of the invention should now become apparent upon a reading of the following detailed description taken in conjunction with the accompanying drawings in which:

FIG. 5A schematically illustrates a bendable section of ribbed construction;

FIG. 5B schematically illustrates a bendable section of bellows construction;

FIG. 5C is a cross-sectional view through a tool motion member illustrating the motion control cables and the tool actuation push rod;

FIG. 8C is a cross-sectional view through the handle motion member of FIG. 8A illustrating the motion control cables and the tool actuation push rod;

FIG. 10A is a schematic diagram of the pivotal pitch jaws and the control handle mechanism that may be used with the embodiments of FIGS. 8A and 9A;

FIG. 10B is a schematic diagram of the mechanism of FIG. 10A showing the upper handle controlling the lower jaw;

FIG. 10C is a schematic diagram of the mechanism of FIG. 10A showing the lower handle controlling the upper jaw;

DETAILED DESCRIPTION OF THE INVENTION

Figure 1:
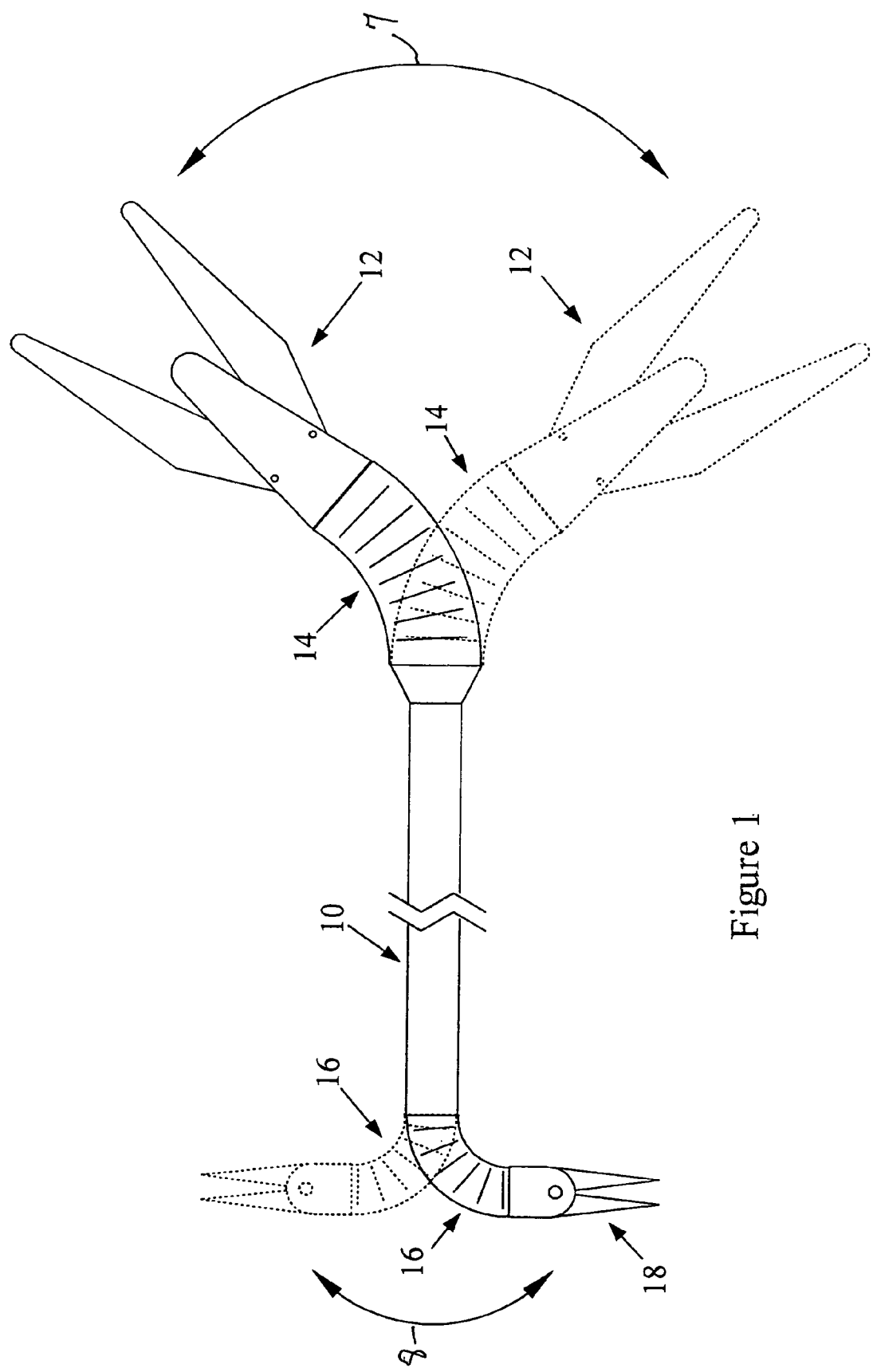
FIG. 1 is a side view of a schematic diagram of a surgical instrument in accordance with the present invention.
Figure 2:
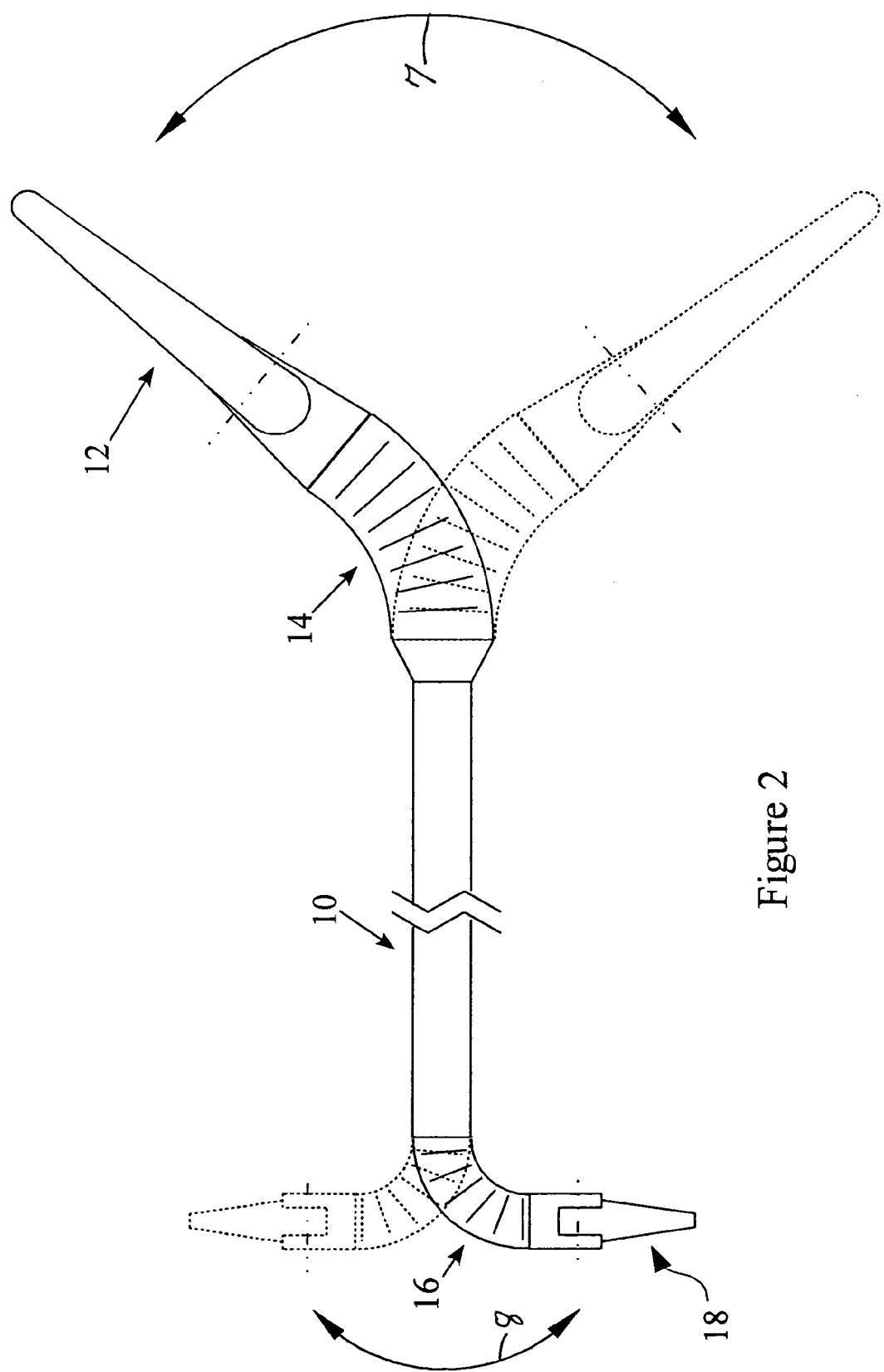
FIG. 2 is a plan view of the instrument shown in FIG. 1.

FIGS. 1 and 2 show respective side and top views of one embodiment of the present invention. Both the tool and the handle motion members are bendable in any directions, and they are connected to each other via cables in such a way that the tool motion member bends in the opposite direction of the handle motion member, thereby creating a sensation that the tool always points in generally the same direction as the handle. Although FIGS. 1 and 2 shows only the side and top views where only pitch and yaw motions are actuated, respectively, it should be noted that the handle motion member could be bent in any direction, actuating the tool motion member to bend in directly opposite directions, and in the same plane. Herein these motion members are also referred to as turnable members. In addition, unlike mechanisms that are comprised of pivotal joints, the bendable motion members can bend in any direction without any singularity. As a result, as shown in FIG. 3, the surgeon is be able to roll the instrument tool 18 about its longitudinal axis 11 at any orientation simply by rolling the handle, a desirable motion for suturing in off-axis.

Figure 3:
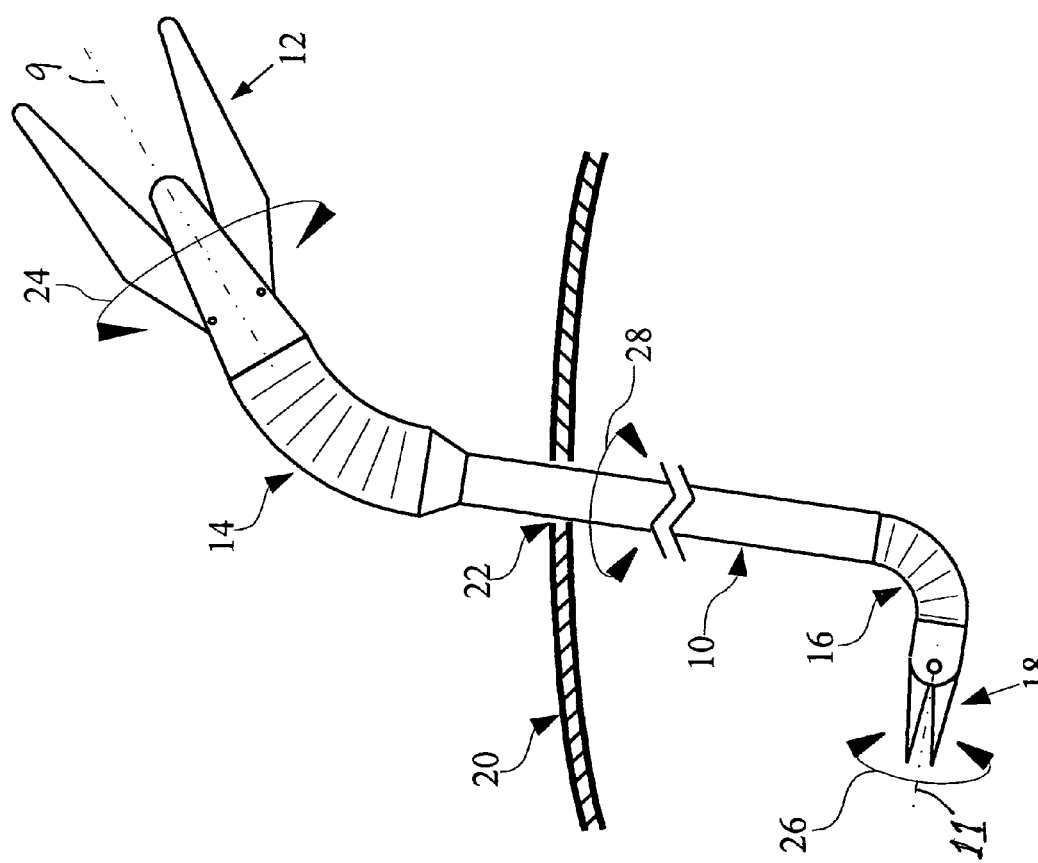
FIG. 3 shows the instrument of FIG. 1 illustrating the roll of the control handle and the attendant roll of the tool end.

Regarding FIGS. 1-3, there is disclosed an instrument that is comprised of an elongated instrument shaft 10 supporting, at its proximal end, the handle 12 connecting with the handle motion member 14. At the distal end of the instrument shaft there is disposed the tool motion member 16 that couples to the tool or end effector 18, shown in FIG. 1 as a set of jaws. It is understood that other types of tools may also be substituted for the jaw set that is illustrated.

In FIGS. 1 and 2 one position is shown in solid outline and an alternate position is shown in dotted outline. These two different positions are also illustrated by the double-headed motion arrow 7 indicating motion of the handle 12 and the double-headed motion arrow 8 indicating corresponding motion of the tool 18.

In the descriptions set out herein the term "bendable section", "bendable segment", "bendable motion member" or "turnable member" refer to an element of the instrument that is controllably bendable in comparison to an element that is pivoted. The bendable elements of the present invention enable the fabrication of an instrument that can bend in any direction without any singularity, and that is further characterized by a ready capability to bend in any direction, all with a single unitary structure. A definition of these bendable motion members is—an instrument element, formed either as a controlling means or a controlled means, and that is capable of being constrained by tension or compression forces to deviate from a straight line to a curved configuration without any sharp breaks or angularity—.

FIG. 3 also illustrates the roll of the instrument made possible by the interaction between the control handle 12 and tool 18, and their respective motion members 14 and 16. The instrument shaft is shown positioned through the incision or aperture 22 in the abdominal wall 20.

This rolling action is also illustrated in FIG. 3 by the series of circular arrows that include arrow 24 illustrating the rotation or rolling of the handle 12 about axis 9 to cause a corresponding rotation or rolling of the tool 18 about axis 11, illustrated by the circular arrow 26. Similarly, the instrument shaft 10 is rotated at the same time, as illustrated by the arrow 28 in FIG. 3.

Figure 4:
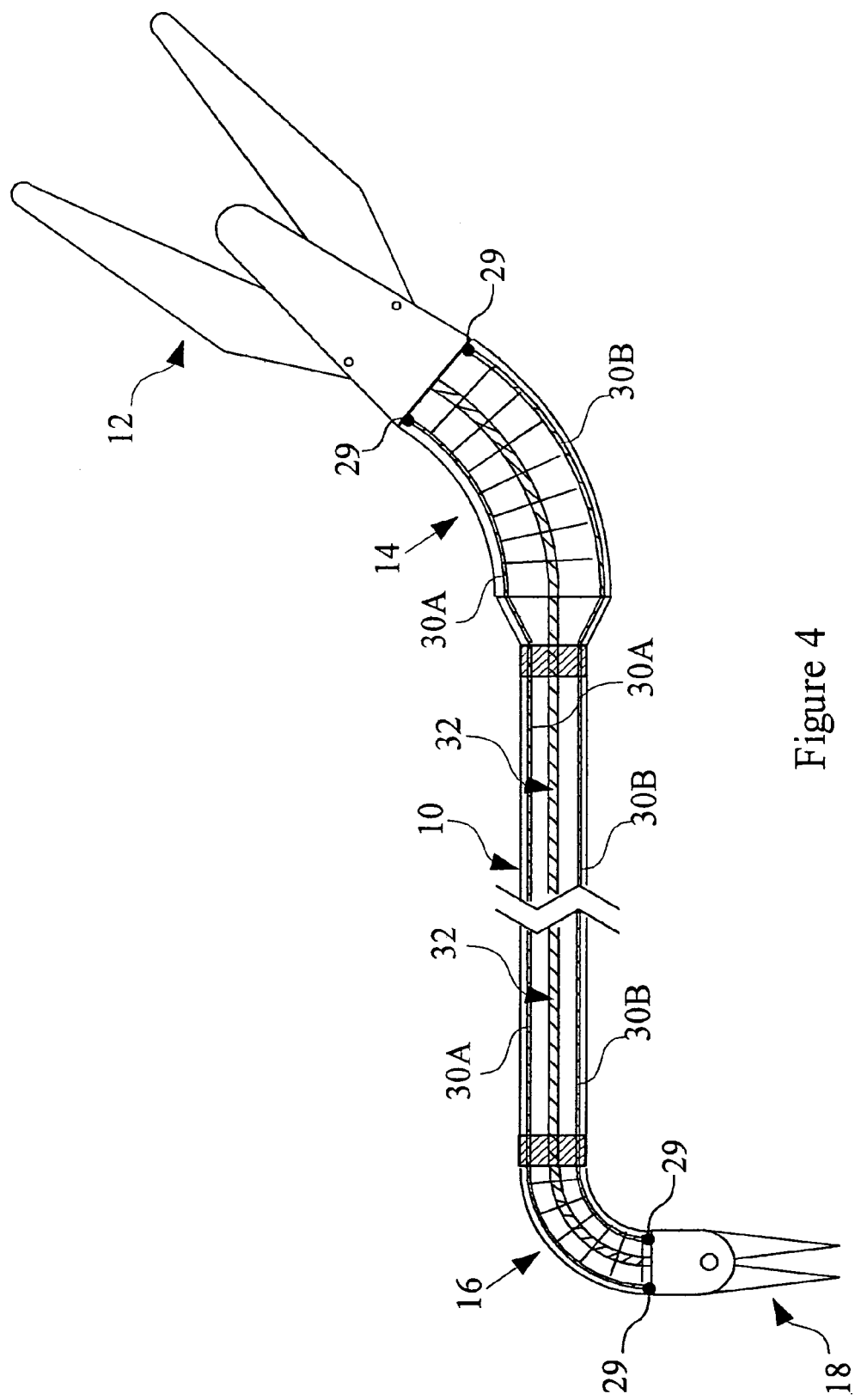
FIG. 4 is a view like that shown in FIG. 1 and additionally illustrating a cabling scheme that can be used in the surgical instrument.

Reference is now made to FIG. 4 that illustrates the internal cabling scheme of the embodiment disclosed in FIGS. 1-3. In FIG. 4 the same reference characters are used as in FIGS. 1-3 to identify like elements. The control cables 30A and 30B run parallel to each other along the longitudinal direction of the instrument shaft 10 and they are terminated, respectively, at the proximal and distal ends of the handle and tool motion members. The termination is shown at each point 29 in FIG. 4 and represents a location where the cable is fixed at each end thereof to the respective handle and tool structures. Although only two motion member control cables 30A and 30B are shown in the FIG. 4, it should be noted that three or more cables are preferred in order to actuate the tool motion member in any direction.

As illustrated in FIG. 4, as an example, when the handle 12 is tilted upwardly by bending the handle motion member 14 upwardly, the proximal end of the cable 30B is pulled while the cable 30A is relaxed. As a result, the distal end of the cable 30B is shortened causing the tool motion member 16 to bend downwardly resulting in a pitching down motion of the tool 18, as illustrated in FIG. 4.

In addition to the motion control cables 30A and 30B, FIG. 4 also illustrates the tool actuating push rod 32 that runs through the center of the motion members 14, 16 and the elongated shaft 10 so that the tool actuation is decoupled from the bending motions of the motion members. Since the sections of the push rod 32 that go through the tool and handle motion members 14, 16 need to bend, the rod 32 needs to be somewhat flexible, and in order to prevent these sections from buckling, they are preferably confined in a conduit or a channel. See the more detailed embodiment in FIGS. 21-23. Alternatively, the section of push rod 32 that does not need to bend may be reinforced to prevent it from buckling. The proximal and distal ends of the push rod 32 are connected to the push-pull handle and jaw mechanisms, respectively (shown in FIGS. 7A-7D).

The bendable handle and tool motion members 14, 16, such as illustrated in FIG. 4 can be constructed in many different embodiments. Refer, for example, to FIGS. 5A and 5B for an illustration of two possible embodiments showing two degrees of freedom (DOF) bending motion members. FIG. 5A shows a ribbed construction that includes alternating ribs 13 and slots 15 disposed about the center column 17. The push rod 32 is disposed at the center of the center column 17. The control cables 30A, 30B extend through the outer portions of the ribs 13.

FIG. 5B shows a bellow construction 13A including a center column 17A which accommodates the push rod 32 at its center. The control cables 30A, 30B extend through the bellows construction 13A. In both cases of FIGS. 5A and 5B, and, as shown in the cross-sectional view of FIG. 5C, the motion control cables 30 extend along the outer edge whereas the push rod 32 is centered along the center column 17. The center column 17, which acts as a conduit for the somewhat flexible push rod 32, is relatively stiff longitudinally (high column strength) in order to maintain the overall length of the motion cable pathways constant, while maintaining lateral flexibility for bending. It should be noted that a variety of geometries may be employed for the bending motion member construction for improved lateral flexibility and column/torsion stiffness.

Figure 6:
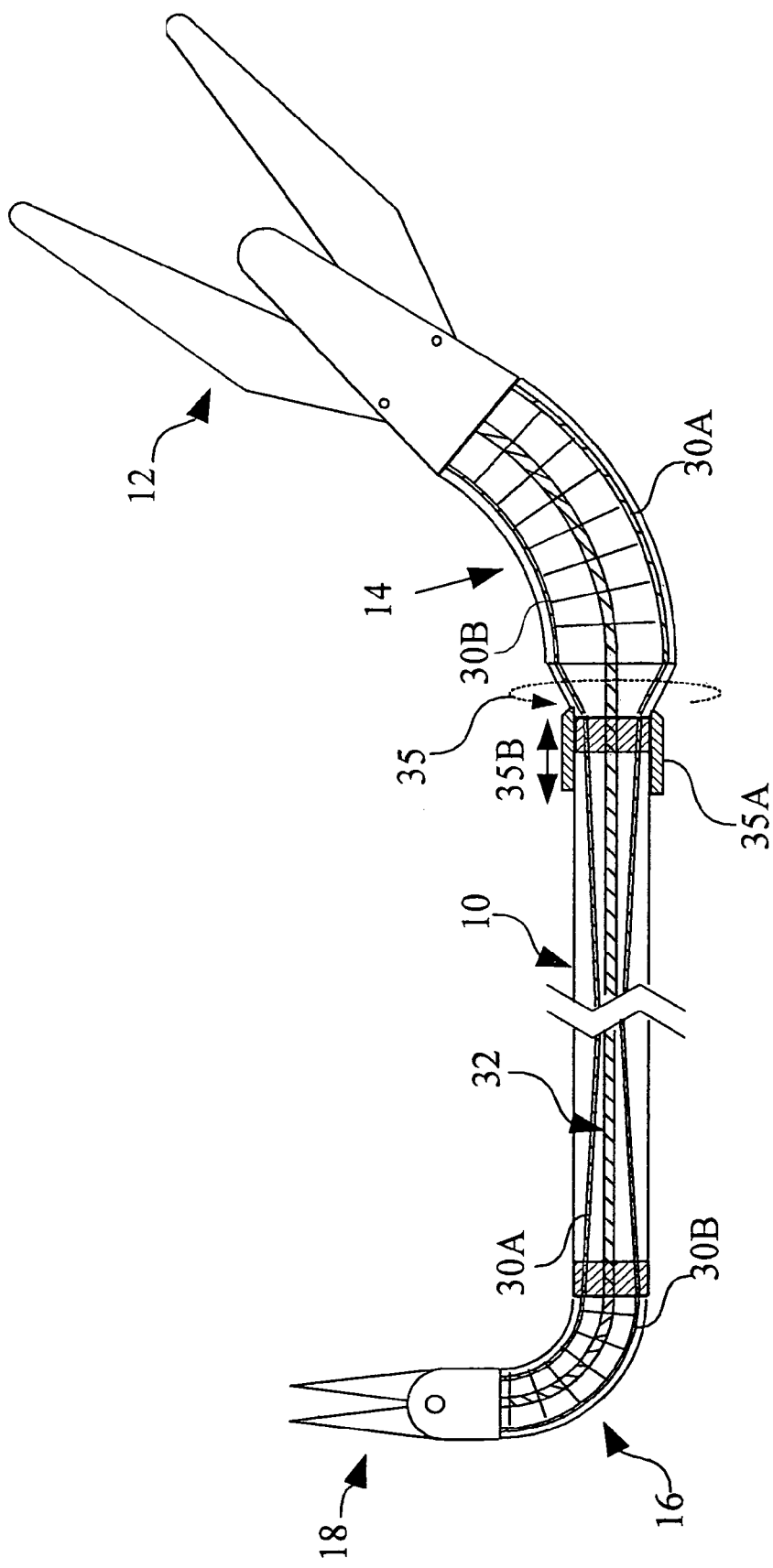
FIG. 6 is a schematic diagram like that shown in FIG. 1 but where the handle to tool motion is opposite to that illustrated in FIG. 1.

FIG. 6 illustrates another embodiment of the present invention where the axial orientation of the handle with respect to the elongated instrument shaft is changed. In this embodiment, the surgeon, before or in the middle of the surgical procedure, may unlock, rotate axially and then lock back the handle onto the elongated instrument shaft. In FIG. 6 the same reference characters are used as in FIG. 4 to designate like elements. Regarding FIG. 6, there is disclosed an instrument that is comprised of an elongated instrument shaft 10 supporting, at its proximal end, the handle 12 connecting with the handle motion member 14. At the distal end of the instrument shaft there is disposed the tool motion member 16 that couples to the tool or end effector 18, shown as a set of jaws. In FIG. 6, because the handle has been rotated, the control cables 30A and 30B are shown in a crossed orientation. Also, terminations are used on the cable ends as shown before in FIG. 4.

As illustrated in FIG. 6, the handle motion member 14 may be axially rotatable 180 degrees from its normal orientation, such as was previously illustrated in FIG. 4. This is illustrated in FIG. 6 by the rotation arrow 35 that is shown extending about the rotation and locking member 35A, which slides in the direction of arrow 35B to lock and unlock the axial orientation of the handle motion member 14 with respect to that of the elongated shaft 10. As a result, when the handle is tilted upwardly, cable 30A is pulled instead of cable 30B, therefore, pitching the tool upwardly rather than downwardly, as shown in FIG. 6. This feature may be very useful when the surgeon's hand is in awkward position.

Figure 7A:
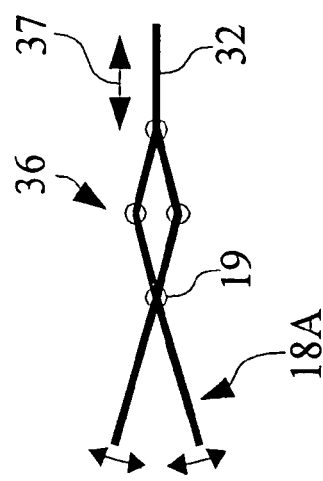
FIG. 7A is a schematic diagram of a tool push-pull arrangement that employs a four bar mechanism.
Figure 7B:
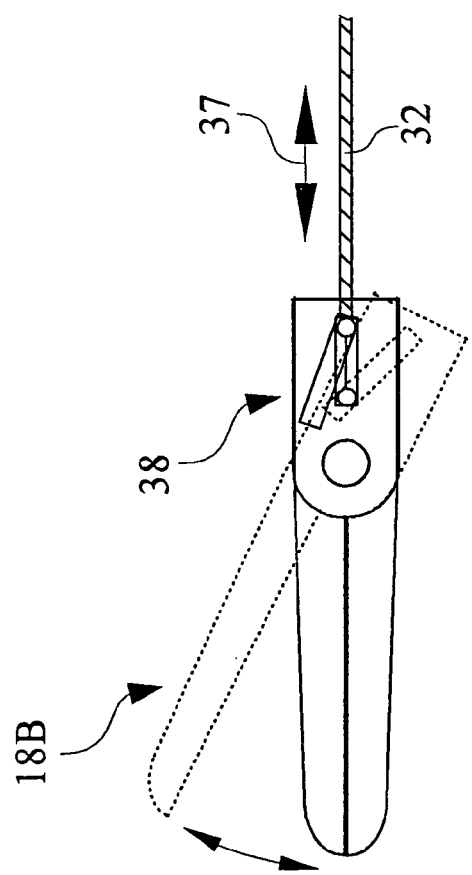
FIG. 7B is a schematic diagram of a tool push-pull arrangement that employs a camming slot mechanism.

FIGS. 7A-7D illustrate some examples of push-pull jaw and handle mechanisms that may be employed with the present invention. For example, FIGS. 7A and 7B show two jaw constructions, one based on a four bar mechanism and the other based on a camming slot mechanism. It is noted that, in addition to the illustrated embodiments, a wide variety of similar push-pull or other mechanisms may be readily adapted to the tool end of the instrument of the present invention. For instance, one can adapt a stapler or clip applier tool to this invention. In addition to tool configurations described above, energy delivering tools such as monopolar, bipolar and electrocautery tools and non-actuated tools such as a scalpel or monopolar j-hook can be readily employed.

FIG. 7A schematically illustrates the four bar mechanism 36 operated from the push rod 32 and coupling to the jaws 18A at the jaw axis 19. FIG. 7B schematically illustrates the camming slot mechanism 38 operated from the push rod 32 and coupling to the jaw arrangement 18B. In either case the linear translation of the push rod 32, indicated by the double headed arrow 37, controls the opening and closing of the jaws.

Figure 7C:
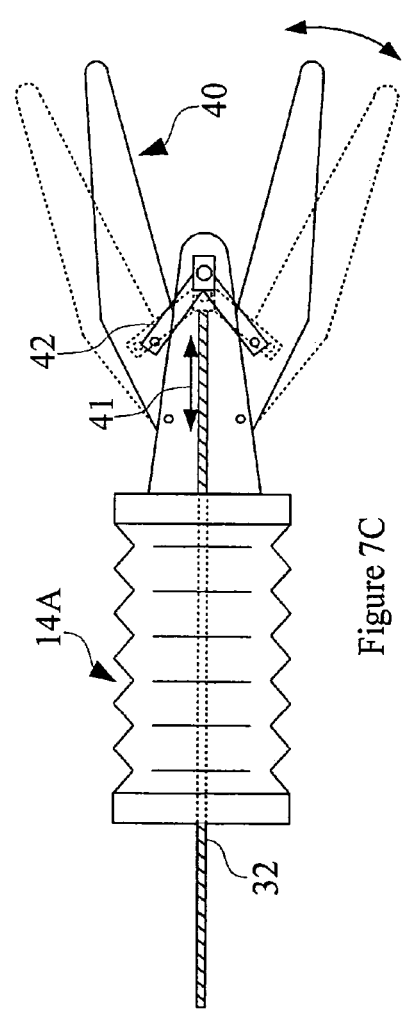
FIG. 7C is a schematic diagram of a handle push-pull arrangement that employs a palm grip based upon a four bar mechanism.
Figure 7D:
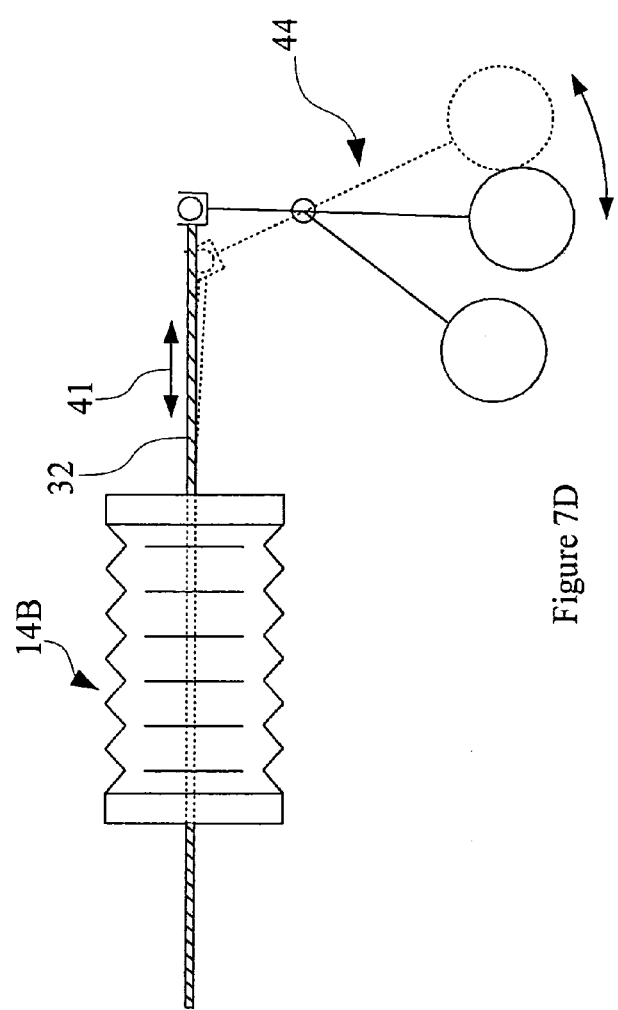
FIG. 7D is a schematic diagram of a handle push-pull arrangement that employs a pistol grip handle.

Similarly, FIGS. 7C and 7D show two examples of common push-pull handle designs; a palm grip in-line handle 40 including a bar mechanism 42 shown in FIG. 7C, and a pistol grip handle 44 shown in FIG. 7D. Again, a wide variety of similar push-pull handle designs may be employed. FIG. 7C illustrates the bar mechanism controlled from the handle 40 to actuate the push rod 32. FIG. 7D illustrates the pistol grip handle 44 for controlling the push rod 32. Double headed arrows 41 indicate the motion occasioned by the handle control on the push rod. FIGS. 7C and 7D also respectively show bellows type wrists 14A and 14B for facilitating corresponding tool motion.

Figure 8A:
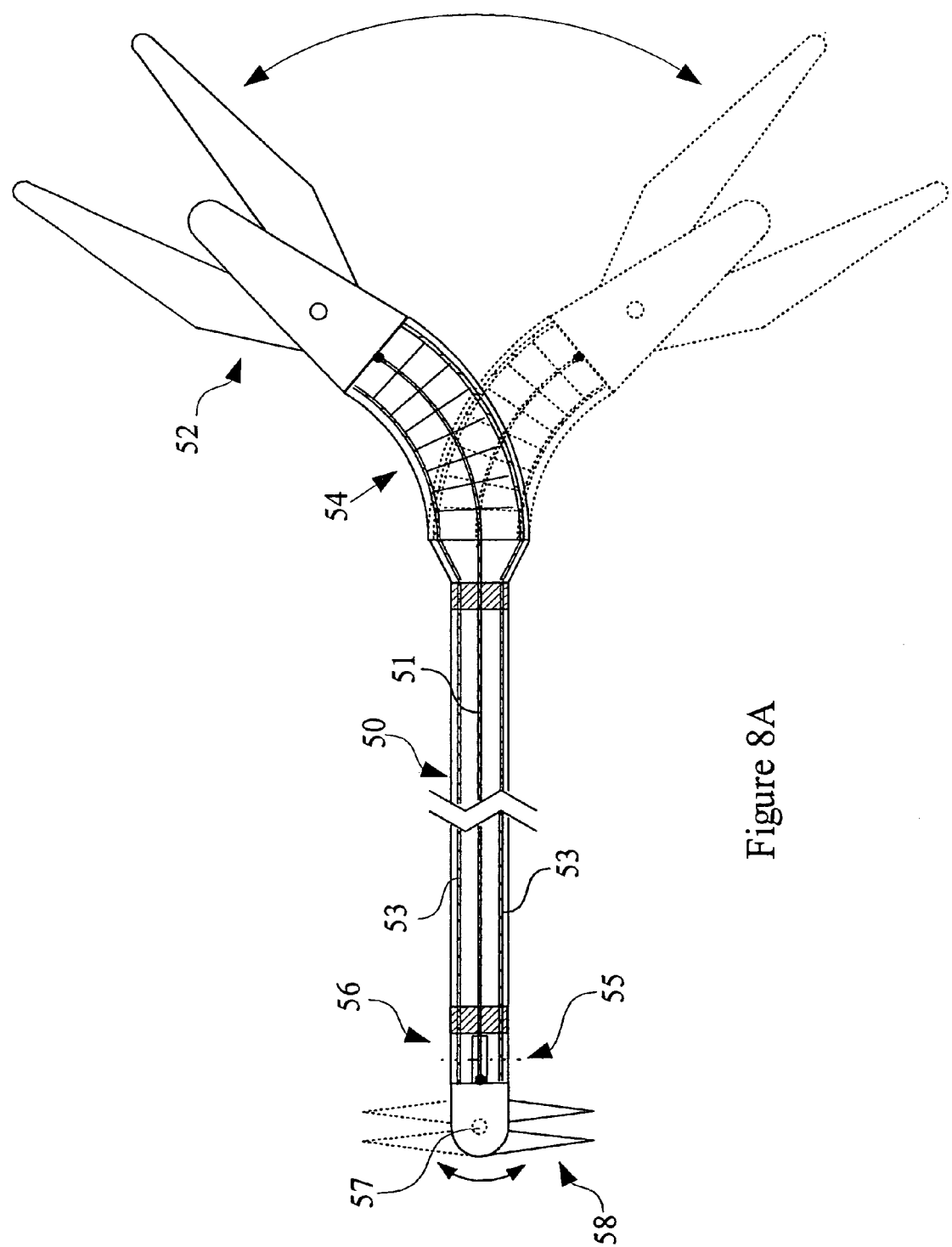
FIG. 8A is a side view of a schematic diagram of a surgical instrument in accordance with another embodiment the present invention where the tool motion member is comprised of two pivotal joints orientated orthogonal to each other while the handle motion member is bendable in any directions, as in previously described embodiments.
Figure 8B:
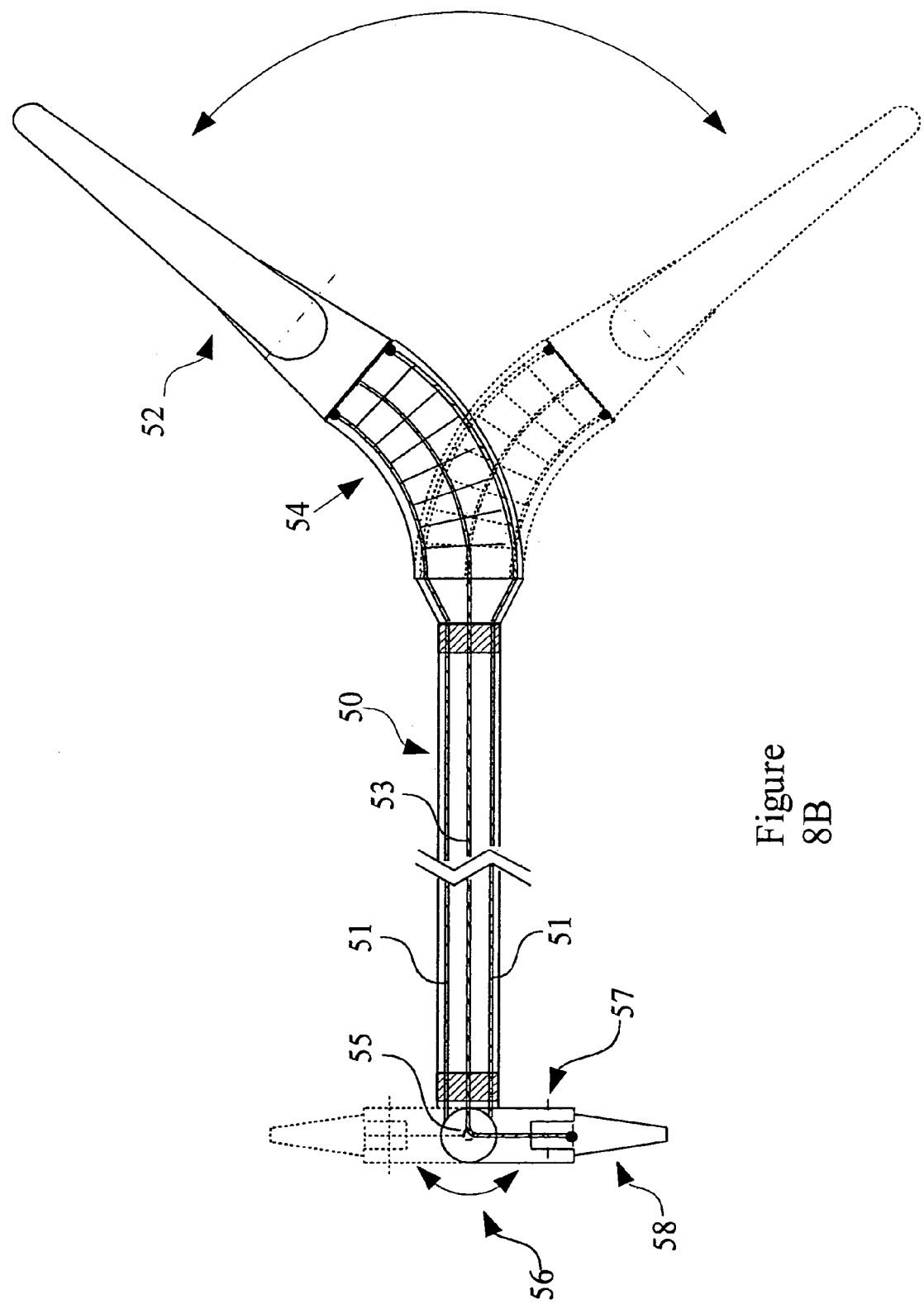
FIG. 8B is a plan view of the instrument shown in FIG. 8A.

FIGS. 8A, 8B and 8C illustrate another embodiment of the present invention where the tool motion member is comprised of two pivotal joints (pitch and yaw axis) orientated orthogonal to each other while the handle motion member is bendable in any direction, as in previously described embodiments. This embodiment relies on independent pitch motions of each jaw of the tool to provide both the jaw grasping and pitch motion, and therefore, it uses two pairs of pitch motion control cables as shown in FIG. 8C. As in previous embodiments, tilting of the handle in the up/down directions causes respective pitching down/up of the tool (FIG. 8A), and the side-to-side motion of the handle results in yaw motion of the tool (FIG. 8B). The motion at any one point in time is usually a combination of pitch and yaw motions.

Regarding FIGS. 8A-8C, there is disclosed an instrument that is comprised of an elongated instrument shaft 50 supporting, at its proximal end, the handle 52 connecting with the handle motion member 54. At the distal end of the instrument shaft there is disposed the tool motion member 56 that couples to the tool or end effector 58, shown as a set of jaws. It is understood that other types of tools may also be substituted for the jaw set that is illustrated. The side view of FIG. 8A and the plan view of FIG. 8B illustrate the handle motion member as being bendable (a bendable section or segment), as in previous embodiments that have been described. However, the tool motion member 56 is comprised of two separate pivot joints orientated orthogonal to each other while the handle motion member is bendable in any direction. The yaw pivot joint is defined at yaw pivotal axis 55, while the pitch pivot joint is defined at pitch pivotal axis 57, one disposed orthogonal to the other. This embodiment uses two pairs of pitch motion control cables 53, and one pair of yaw motion control cables 51, as shown in the cross-sectional view of FIG. 8C.

Figure 9A:
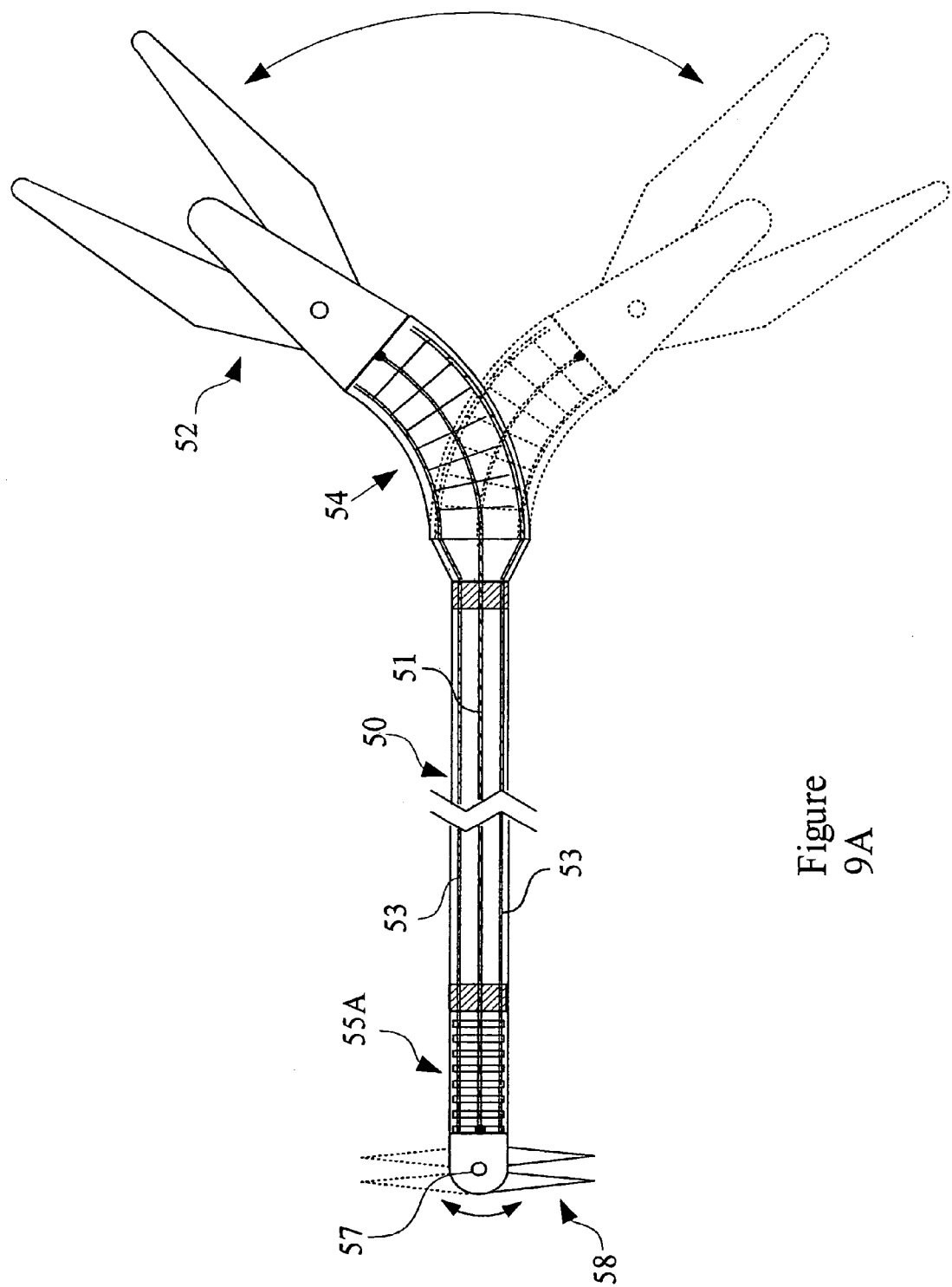
FIG. 9A is a side view of a schematic diagram of a surgical instrument in accordance with still another embodiment the present invention where the tool motion member comprises a pivotal pitch joint as in the previous embodiment (FIG. 8A) but with a bendable section instead of the pivotal joint for the yaw motion.
Figure 9B:
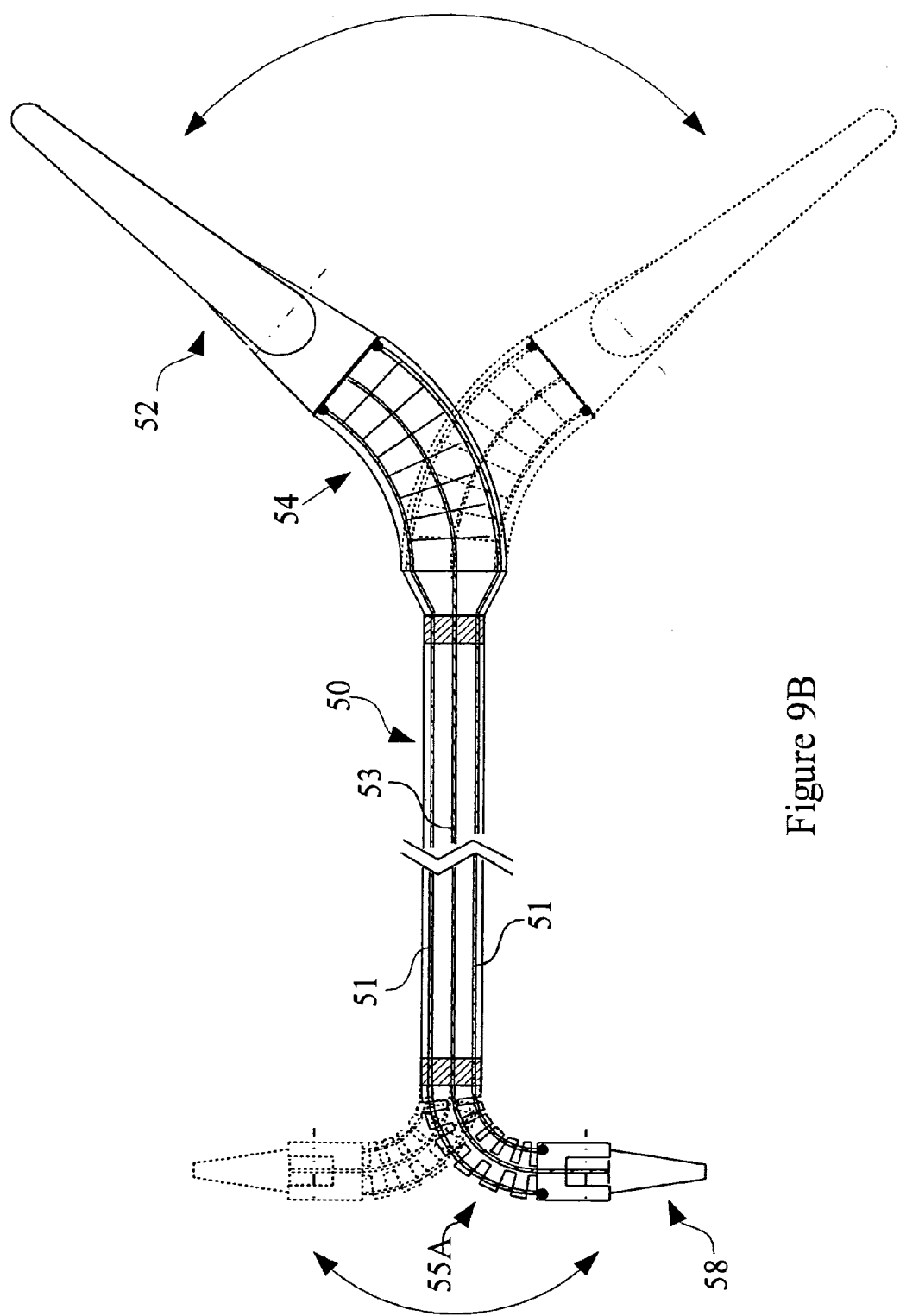
FIG. 9B is a plan view of the instrument shown in FIG. 9A.

FIGS. 9A and 9B show still another embodiment of the tool motion member with a pivotal pitch joint as in the previous embodiment (FIGS. 8A-8C) but with a bendable member 55A instead of the pivotal joint for the yaw motion. As illustrated in FIGS. 9A and 9B, the bendable member 55A bends only in a side-to-side plane (in the plane of the paper in FIG. 9B) providing only the yaw motion of the tool. The pitch motion control cables 53 extend through the central plane of the yaw motion bending section 55A so that the pitch and grip motion of the jaws are decoupled from the yaw motion. The pitch motion control cables 53 control the pivoting at axis 57.

Figure 10D:
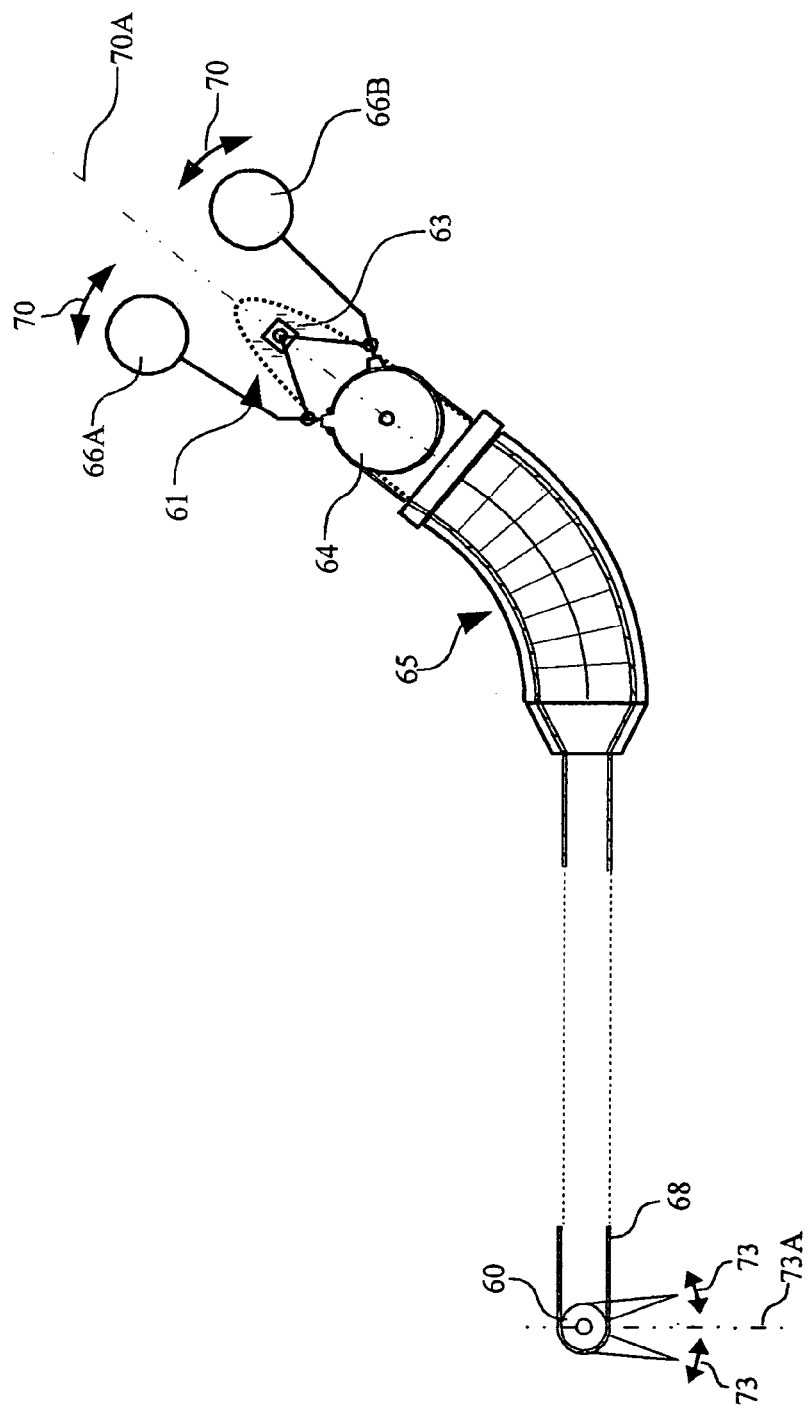
FIG. 10D is a schematic diagram of the mechanism of FIG. 10A illustrating a midline axis of the jaws and the associated control by the bending of the handle motion member.

FIG. 10A is a schematic diagram of the pivotal pitch jaws and the control handle mechanism that may be used with the embodiments of FIGS. 8A and 9A. FIG. 10B is a schematic diagram of the mechanism of FIG. 10A showing the upper handle controlling the lower jaw. FIG. 10C is a schematic diagram of the mechanism of FIG. 10A showing the lower handle controlling the upper jaw. FIG. 10D is a schematic diagram of the mechanism of FIG. 10A illustrating a midline axis of the jaws and the associated control by the bending of the handle motion member.

In FIGS. 10A, 10B and 10C, there is described an example of a cabling/handle mechanism for a set of jaws, and in which the jaws have pivotal pitch motion, as in FIGS. 8 and 9. There are two jaw capstans 60 and two handle capstans 64 as shown in FIGS. 10A-10C. FIG. 10B illustrates the upper handle 66A controlling the lower jaw 18A via the capstan 64A. Alternatively, FIG. 10C illustrates the lower handle 66B controlling the upper jaw 18B via the capstan 64B. FIGS. 10A-10C also show the corresponding cable loops 68 one associated with each jaw. FIG. 10B depicts the cable loop 68A extending about the capstan 64A, through the bendable member 65 and to the jaw capstan 60A for control thereof. FIG. 10C depicts the cable loop 68B extending about the capstan 64B, through the bendable member 65 and to the jaw capstan 60B for control thereof.

The distal end of each of the pitch motion control cable loops 68A, 68B is terminated at the jaw capstan 60A, 60B, and the proximal end of each of the pitch motion control cable loops 68A, 68B is terminated at the handle capstan 64A, 64B. Each handle 66A, 66B is firmly attached to its associated handle capstan 64A, 64B, and the handle capstans are arranged to form a four bar mechanism 61 where the sliding member 63 thereof is constrained to a linear motion along the longitudinal axis of the base 69 of the handle. In FIGS. 10A-10C the various element motions are depicted by double headed arrows; arrows 70 depicting the handle motion; arrows 71 depicting the linear slider motion; arrows 72 depicting the capstan rotation motion; and arrows 73 depicting the jaw rotation occasioned by the jaw capstan rotation motion.

FIG. 10D illustrates the embodiment of FIG. 10A, the motion of the handles at their midline 70A and the corresponding motion of the jaws at their midline 73A. The pitching motion or rotation of the midline 73A of the jaws is controlled by the bending up/down movement of the handle motion member 65. The opening and closing of the handles 66A, 66B relative to midline 70A controls the jaw opening and closing with respect to the jaws midline 73A; as illustrated in FIG. 10D.

The embodiments described so far have employed a handle motion member arrangement that is bendable in any directions. However, just as a variety of tool motion members can be employed, other handle motion types can also be used. For example, FIGS. 11A and 11B show an embodiment with a yaw motion-only bending member for both the tool and handle motion members while pivotal pitching motion of the handles controls pivotal pitching motion of the tool.

Figure 11A:
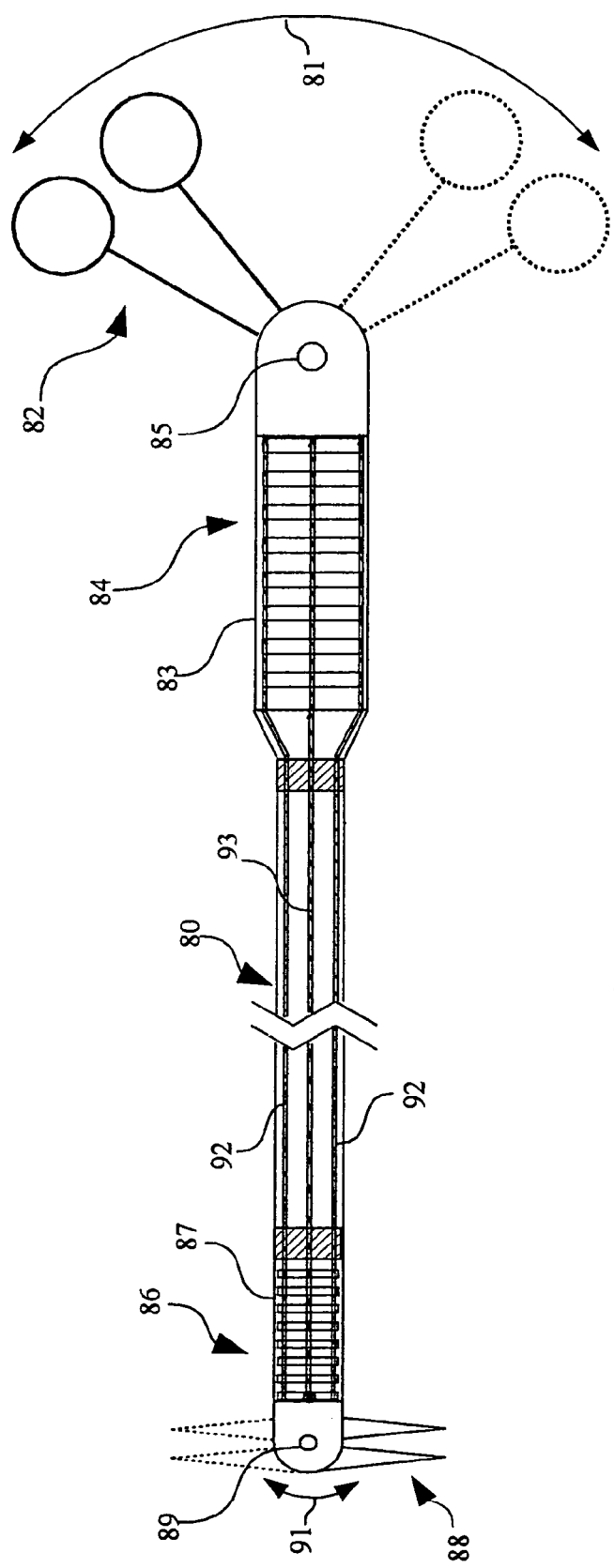
FIG. 11A is a schematic diagram showing an embodiment with yaw motion-only bending members for both the tool and handle motions where pivotal pitching motion of the handle controls pivotal pitching motion of the tool.
Figure 11B:
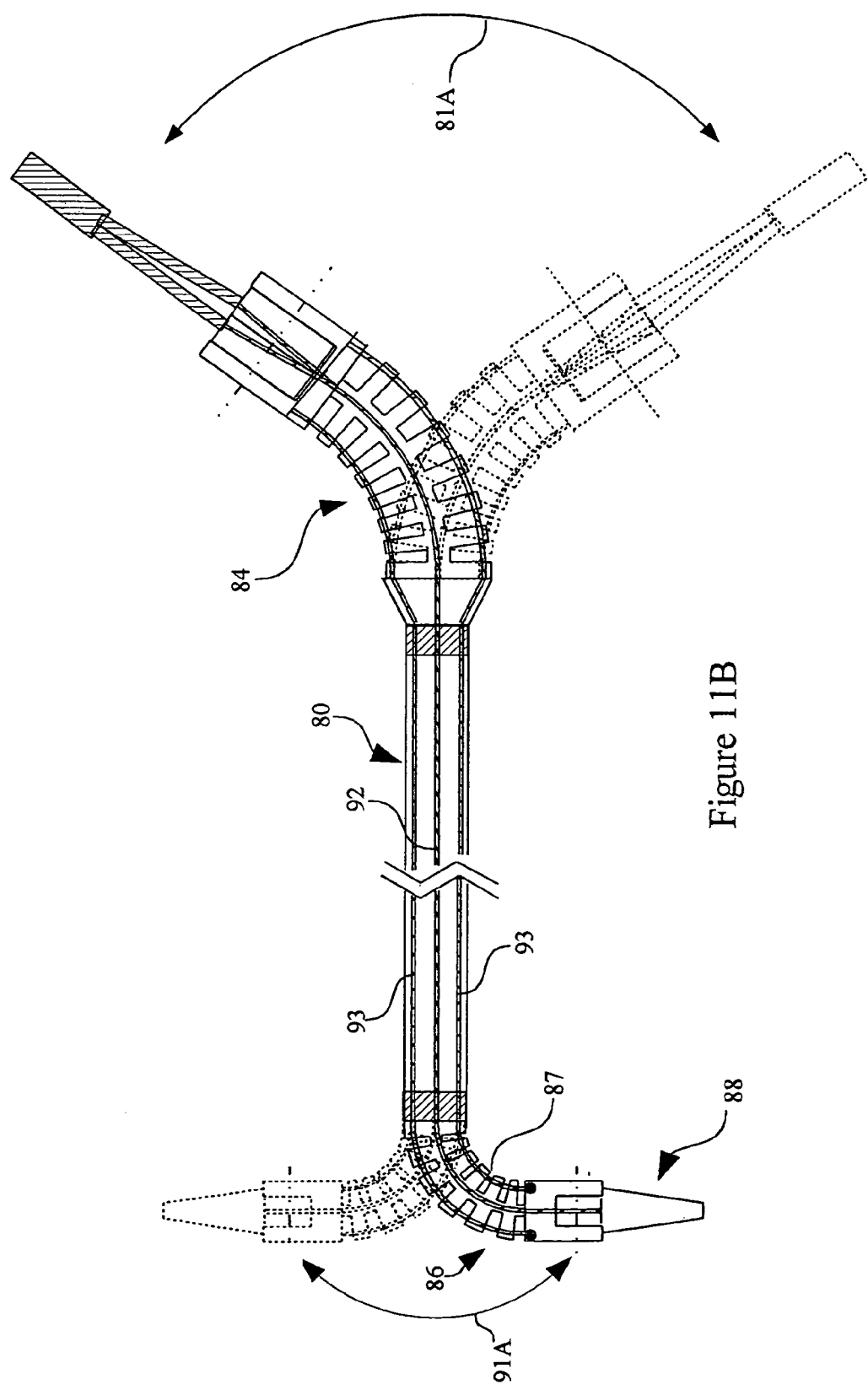
FIG. 11B is a plan view of the instrument shown in FIG. 11A.

FIG. 11A is a schematic diagram showing an embodiment with yaw motion-only bending members for both the tool and handle motions where pivotal pitching motion of the handles controls pivotal pitching motion of the tool. FIG. 11B is a plan view of the instrument shown in FIG. 11A. Regarding FIGS. 11A and 11B, there is disclosed an instrument that is comprised of an elongated instrument shaft 80 supporting, at its proximal end, a handle 82 connecting with a handle motion member 84. The handle 82 is depicted as a hand-held scissors type handle that may be moved in the direction indicated by double headed arrow 81. At the distal end of the instrument shaft 80 there is disposed a tool motion member 86 that couples to a tool or end effector 88, shown in FIG. 11A as a set of jaws.

The handle motion member 84 may be considered as comprised of two components including a bendable segment 83 and a pivotal joint 85. The bendable segment 83 is limited in motion so as to control only yaw motion of the handle. This yaw motion is illustrated by the double headed arrow 81A in FIG. 11B. The pitch motion is defined as motion about pivotal joint 85. This pitch motion is illustrated by the double headed arrow 81 in FIG. 11A. Similarly, at the distal end of the instrument the tool motion member 86 may be considered as comprised of two components including a bendable segment 87 and a pivotal joint 89. The bendable segment or section 87 is limited in motion so as to control only yaw motion of the tool. This yaw motion is illustrated by the double headed arrow 91A in FIG. 11B. The pitch motion is defined as motion about pivotal joint 89. This pitch motion is illustrated by the double headed arrow 91 in FIG. 11A. FIGS. 11A and 11B also depict the control cables for both pitch and yaw. These are illustrated as pitch motion control cables 92 and yaw motion control cables 93. There is preferably a pair of yaw motion control cables and two pairs of pitch motion control cables, one for each jaw.

Figure 12:
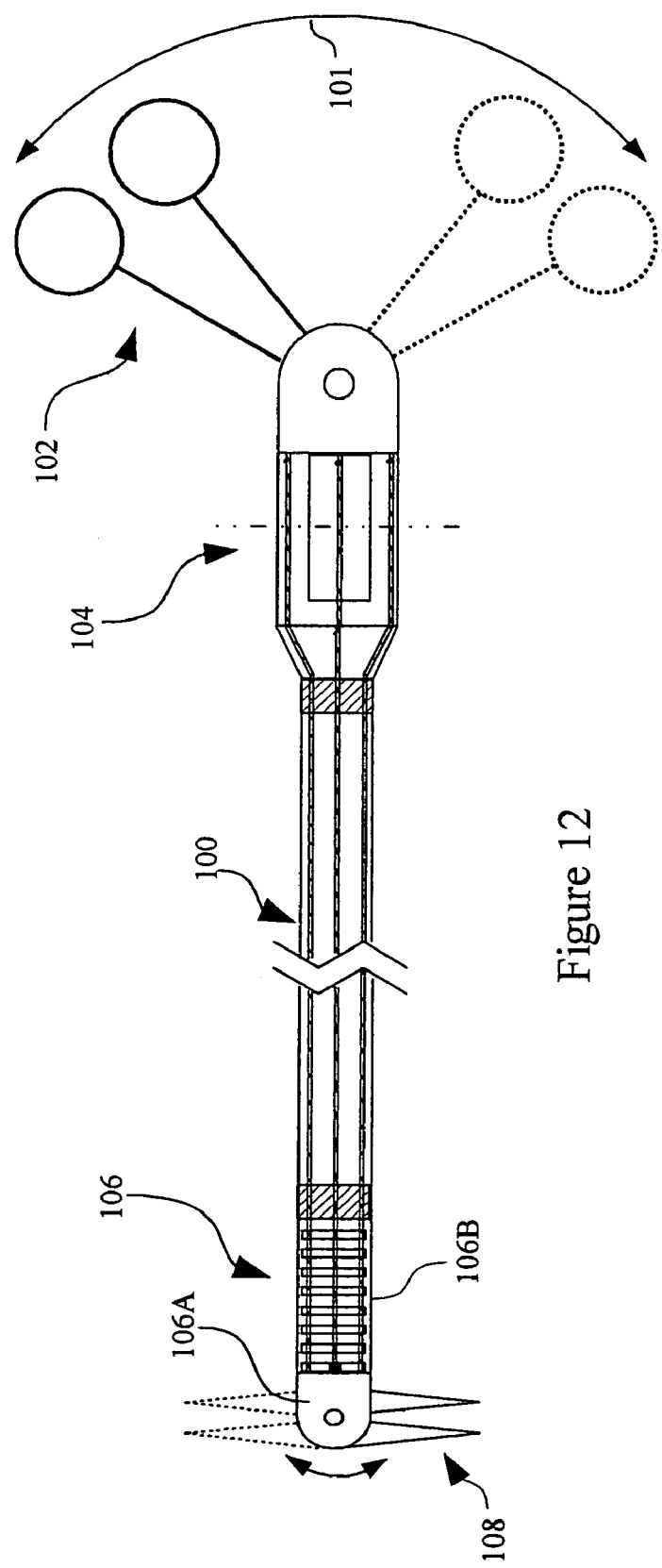
FIG. 12 is a schematic diagram showing an embodiment with one pivotal tool motion joint, one bendable tool motion section, and two pivotal handle motion joints.
Figure 13:
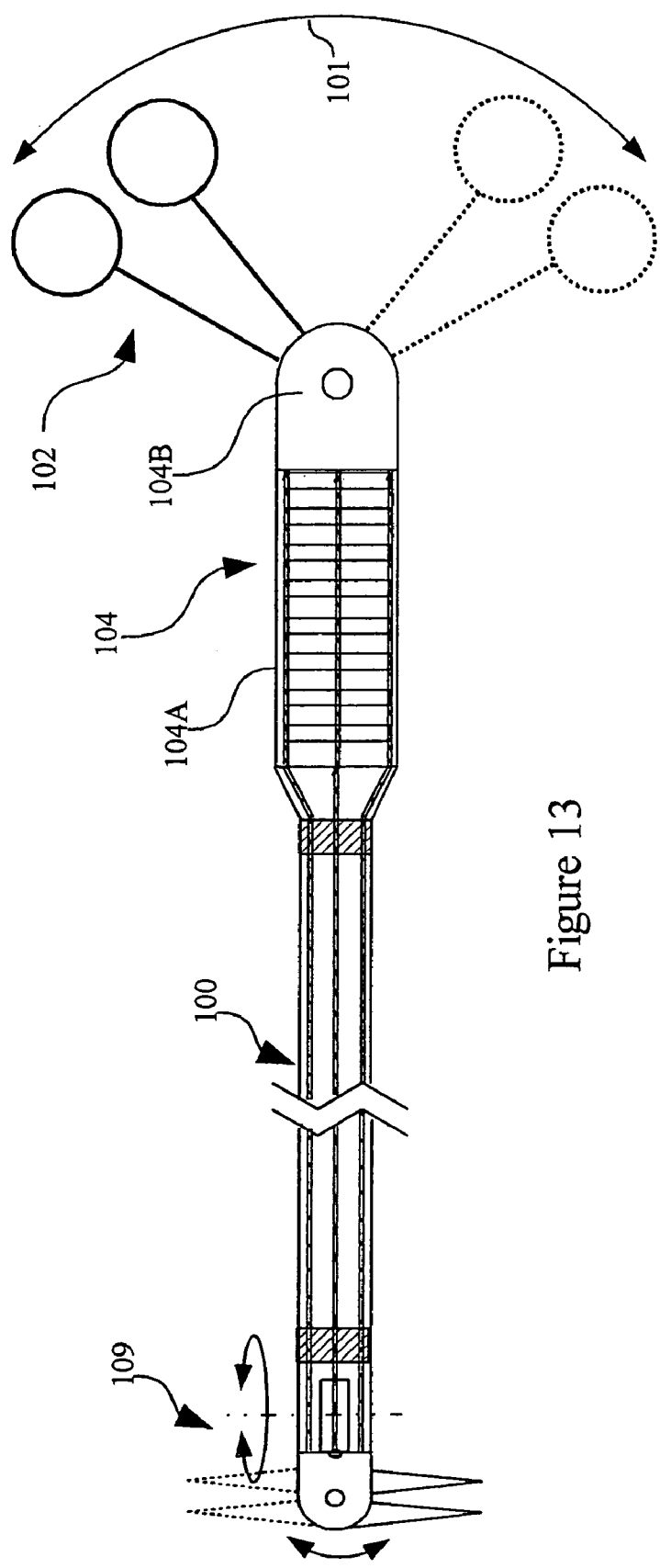
FIG. 13 is a schematic diagram showing an embodiment with two tool motion pivots, and with one bendable section and one pivotal handle motion member.

Other tool and handle motion joint combinations can also be considered as illustrated in FIGS. 12 and 13. In these figures there is disclosed an instrument that is comprised of an elongated instrument shaft 100 supporting, at its proximal end, a handle 102 connecting with a handle motion member 104. In both embodiments the handle 102 is depicted as a hand-held scissors type handle that may be moved in the direction indicated by double headed arrow 101. At the distal end of the instrument shaft 100 there is disposed a tool motion member 106 that couples to a tool or end effector 108, shown in FIGS. 12-14 as a set of jaws.

FIG. 12 shows an embodiment with the tool and handle motion members 106, 104 comprised of one pivotal tool motion joint 106A, one bendable section 106B and two pivotal handle motion joints, respectively. FIG. 13 illustrates an embodiment with two pivotal tool motion joints 109, one bendable section 104A at the handle, and one pivotal handle motion joint 104B.

Figure 14:
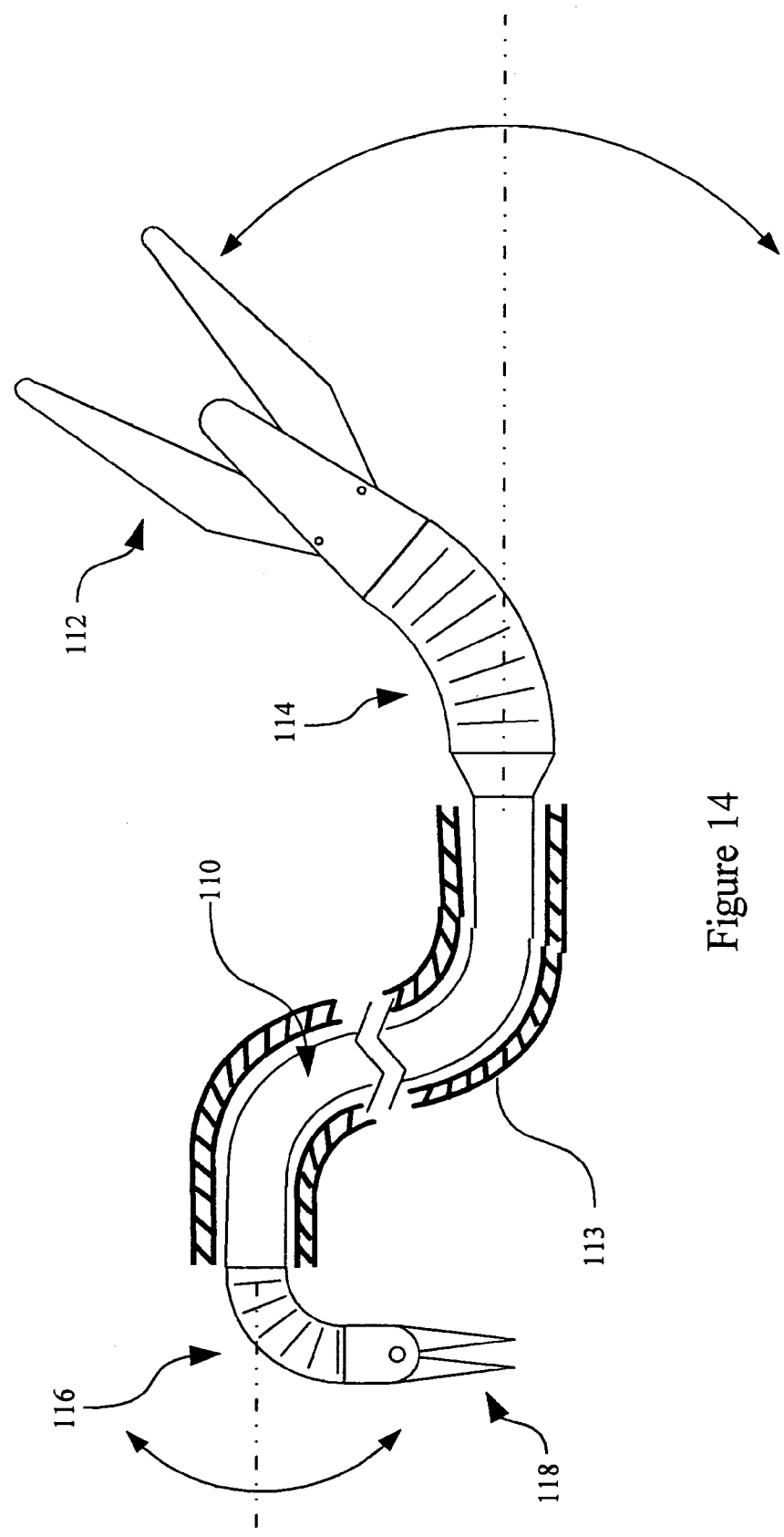
FIG. 14 is a schematic diagram of a further embodiment of the invention in which the instrument shaft, between control and working ends of the instrument, is flexible so as to conform to the shape of an anatomic channel or lumen.

The embodiments described thus far have shown the elongated shaft to be rigid, however, in other embodiments of the invention the shaft may be an elongated flexible shaft. One such embodiment is shown in FIG. 14. The flexible elongated shaft section 110 is generally passive, conforming to the shape of an anatomic channel or body lumen, illustrated in FIG. 14 at 113. There is disclosed an instrument that is comprised of an elongated flexible instrument shaft 110 supporting, at its proximal end, the handle 112 connecting with the handle motion member 114. At the distal end of the flexible instrument shaft 110 there is disposed the tool motion member 116 that couples to the tool or end effector 118, shown in FIG. 14 as a set of jaws.

Figure 15:
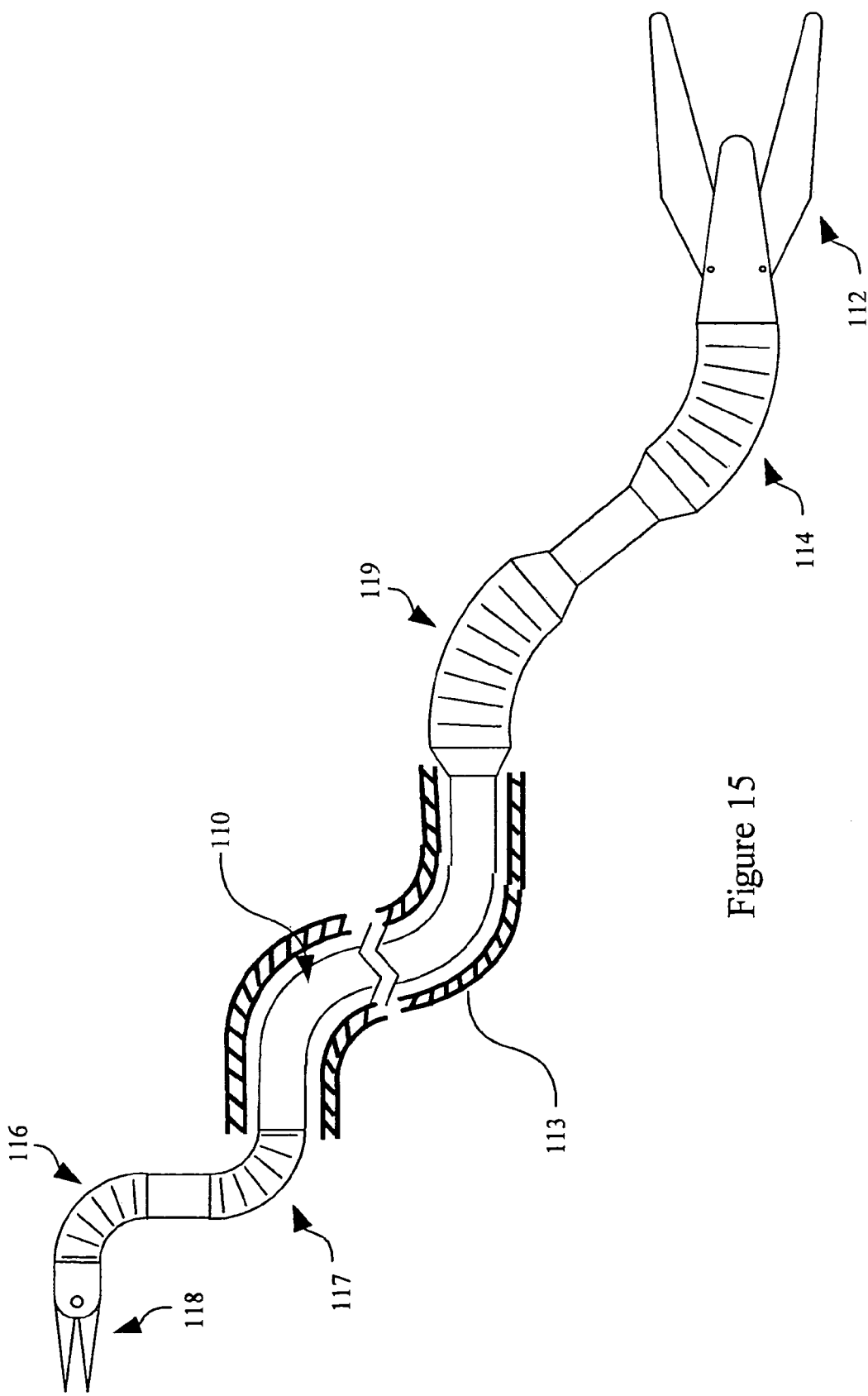
FIG. 15 is a schematic diagram similar to that shown in FIG. 14 where multiple motion members are placed along the length of the elongated instrument shaft for multi-modal controlled movement of the tool.

In addition, one could also have embodiments where multiple motion members are placed along the length of the elongated shaft for multi-modal controlled movement of the tool, as illustrated in FIG. 15. In FIG. 15 some of the same reference characters are used as used in FIG. 14. Thus, this embodiment includes an elongated flexible instrument shaft 110 supporting, at its proximal end, the handle 112 connecting with the handle motion member 114. At the distal end of the instrument there is disposed the tool motion member 116 that couples to the tool or end effector 118, shown in FIG. 15 as a set of jaws. FIG. 15 shows the added bendable sections, bendable segments or bendable motion members 117 and 119 directly at opposite ends of the flexible section 110. The interconnection between the members 116 and 117 may also be a flexible section. Likewise, the interconnection between the members 114 and 119 may be a flexible section. The handle motion members 114 and 119 may be cabled to control the motion of the tool motion members 116 and 117, respectively, or vice versa.

Figure 16:
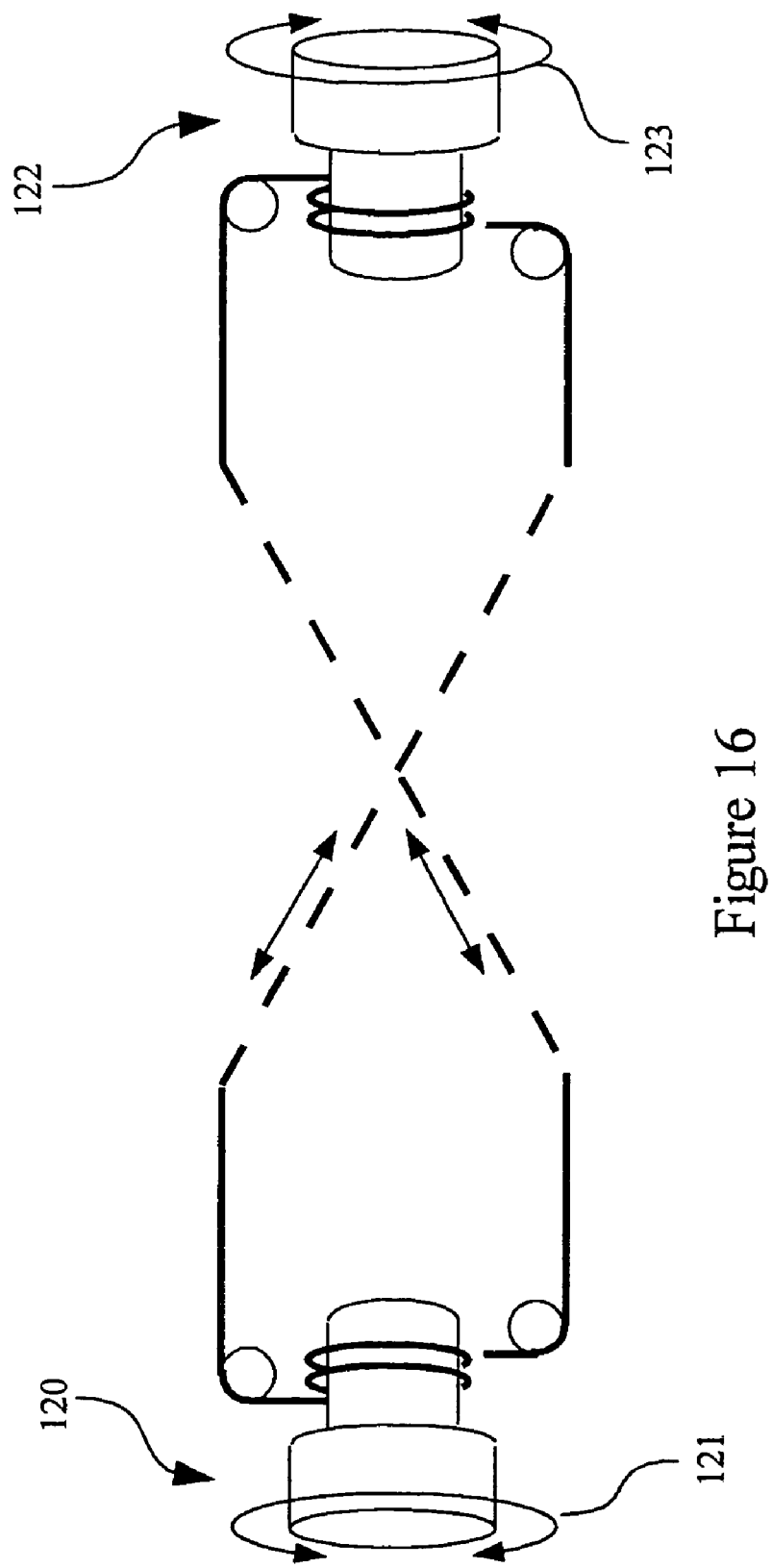
FIG. 16 is a schematic diagram of another embodiment of the present invention in which an axial torque rotation and transmission mechanism is employed.

In some applications such as in lower GI procedures, the elongated shaft may bend at multiple points, and transmitting axial rotational motion about the shaft may be difficult. In such cases, it is more effective to employ a torque transmission mechanism, as illustrated schematically in FIG. 16. FIG. 16 schematically illustrates an axial rotation transmission mechanism that has a tool end 120 and a control handle end 122. A rotation at the handle end 122 converts into a like rotation of the instrument at the tool end 120. This rotation is indicated by the respective arrows 121 and 123.

Figure 17A:
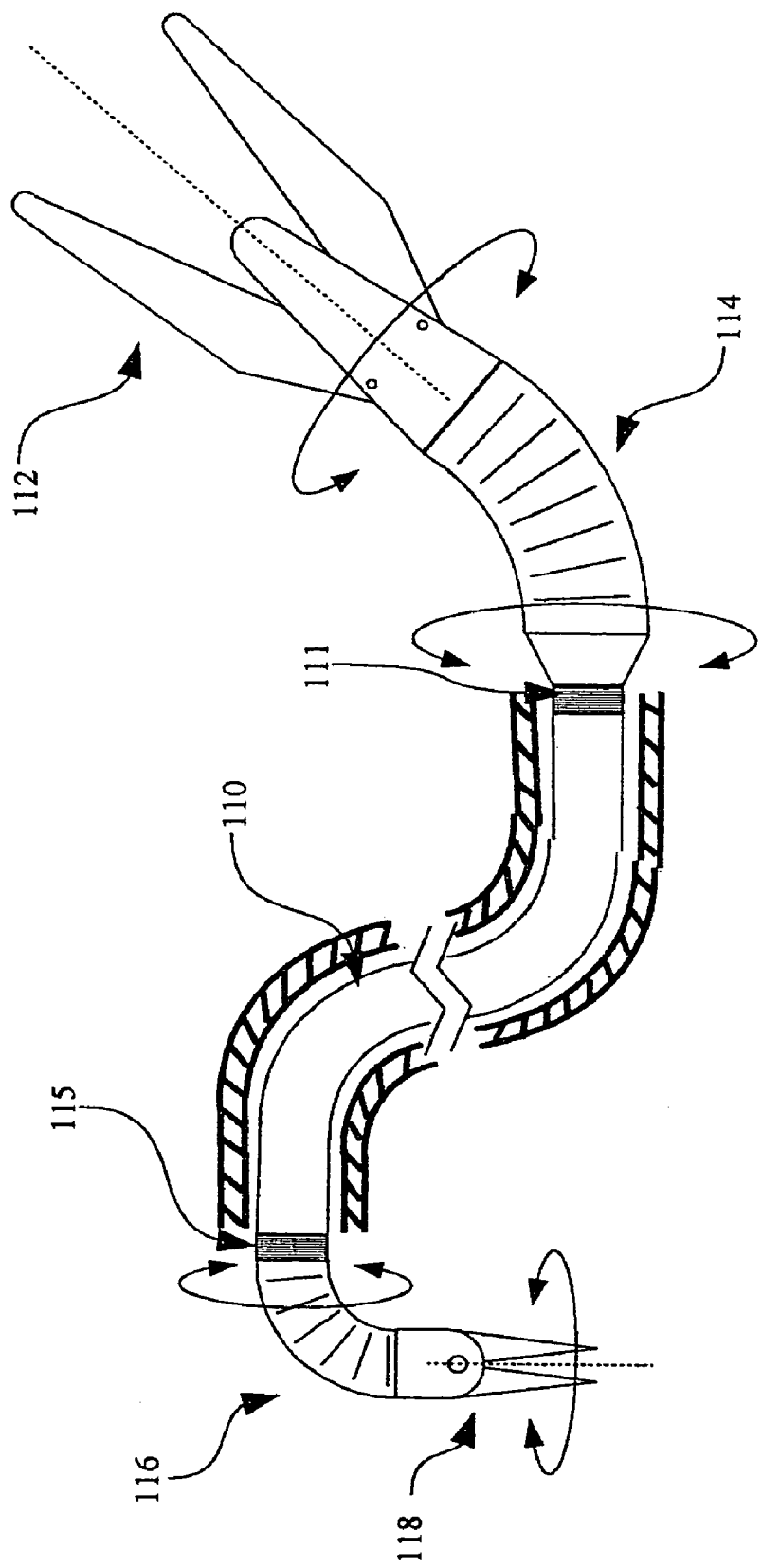
FIGS. 17A and 17B are schematic diagrams relating to FIG. 16 showing alternate embodiments utilizing axial rotation joints at both control and tool ends of the instrument.
Figure 17B:
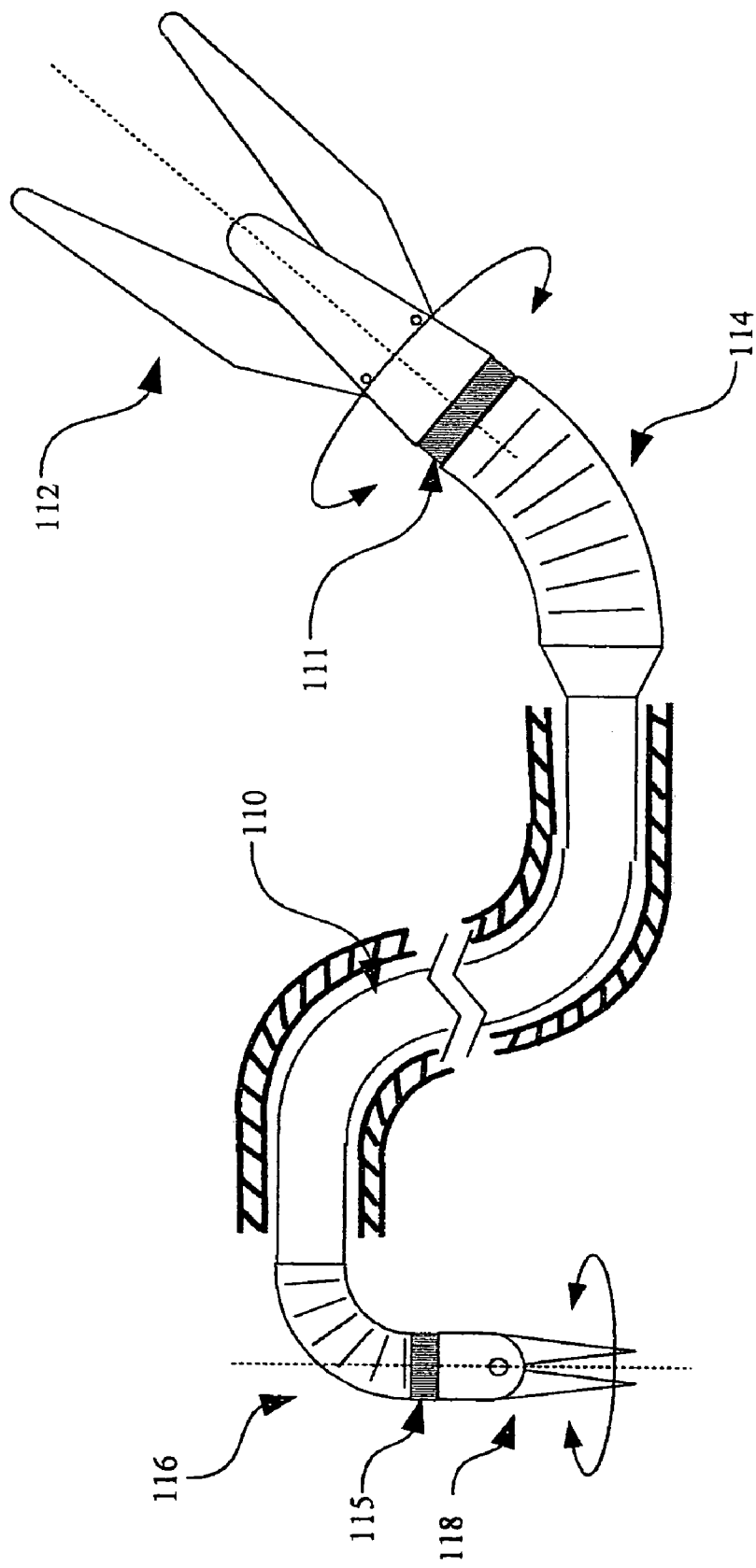

FIGS. 17A and 17B show embodiment of the instrument of the present invention that utilize the schematic concepts of FIG. 16. In FIG. 17 some of the same reference characters are used as used in FIG. 14. Thus, this embodiment includes an elongated flexible instrument shaft 110 supporting, at its proximal end, the handle 112 connecting with the handle motion member 114. At the distal end of the instrument there is disposed the tool motion member 116 that couples to the tool or end effector 118, shown in FIGS. 17A and 17B as a set of jaws. In the embodiment shown in FIG. 17A, there is an axial rotation joint 111 between the proximal end of section 110 and the handle motion member 114, and likewise, there is an axial rotation joint 115 between the more distal end of the section 110 and the tool motion member 116. On the other hand, in the embodiment shown in FIG. 17B, the axial rotation joint 111 is situated between the handle motion member 114 and the handle 112 whereas the axial rotation joint 115 is situated between the tool motion joint 116 and the tool 118. In both cases, these axial rotation joints are interconnected so that rotation of joint 111 causes a corresponding rotation of joint 115. The elongated flexible shaft 110 preferably does not rotate axially itself.

Figure 18:
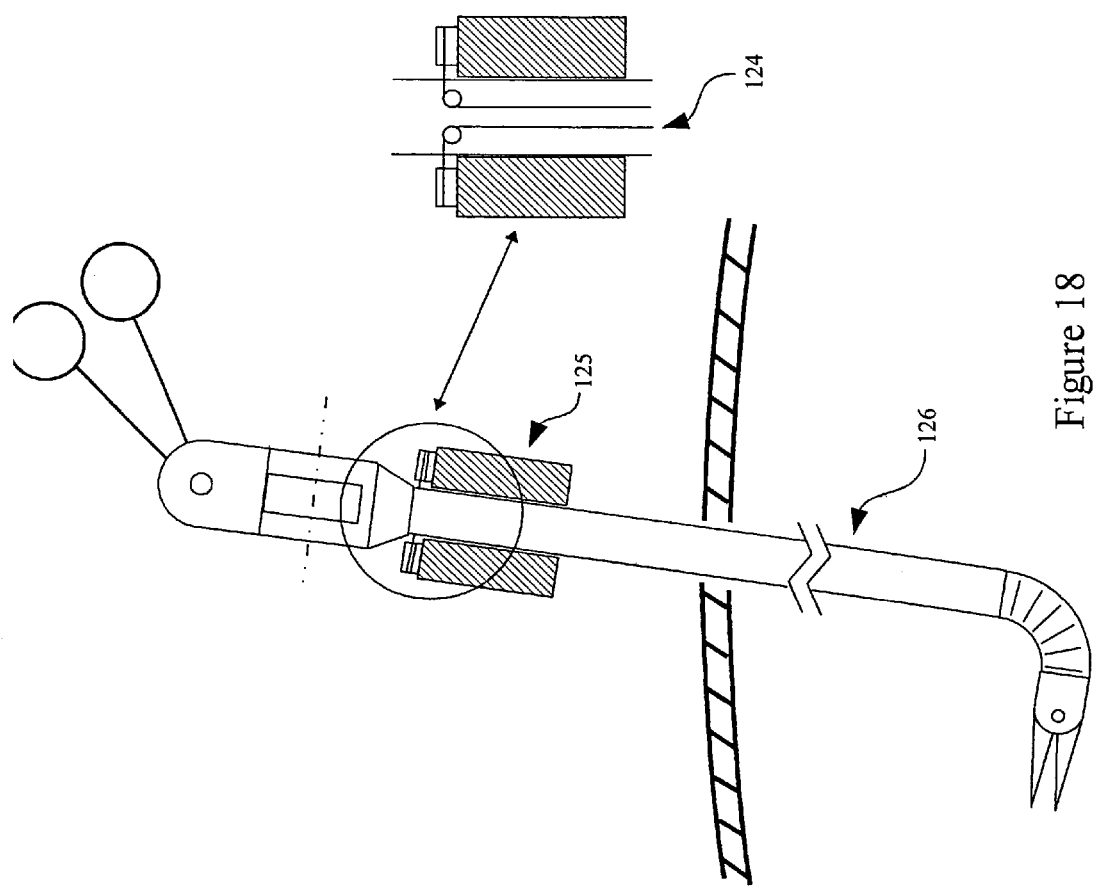
FIG. 18 shows an embodiment in which the tool motion control cables and grip actuation rod are driven an by electrical motors mounted on the side of the proximal end of the elongated instrument shaft instead of being driven directly by the handle motion member and handle.
Figure 19:
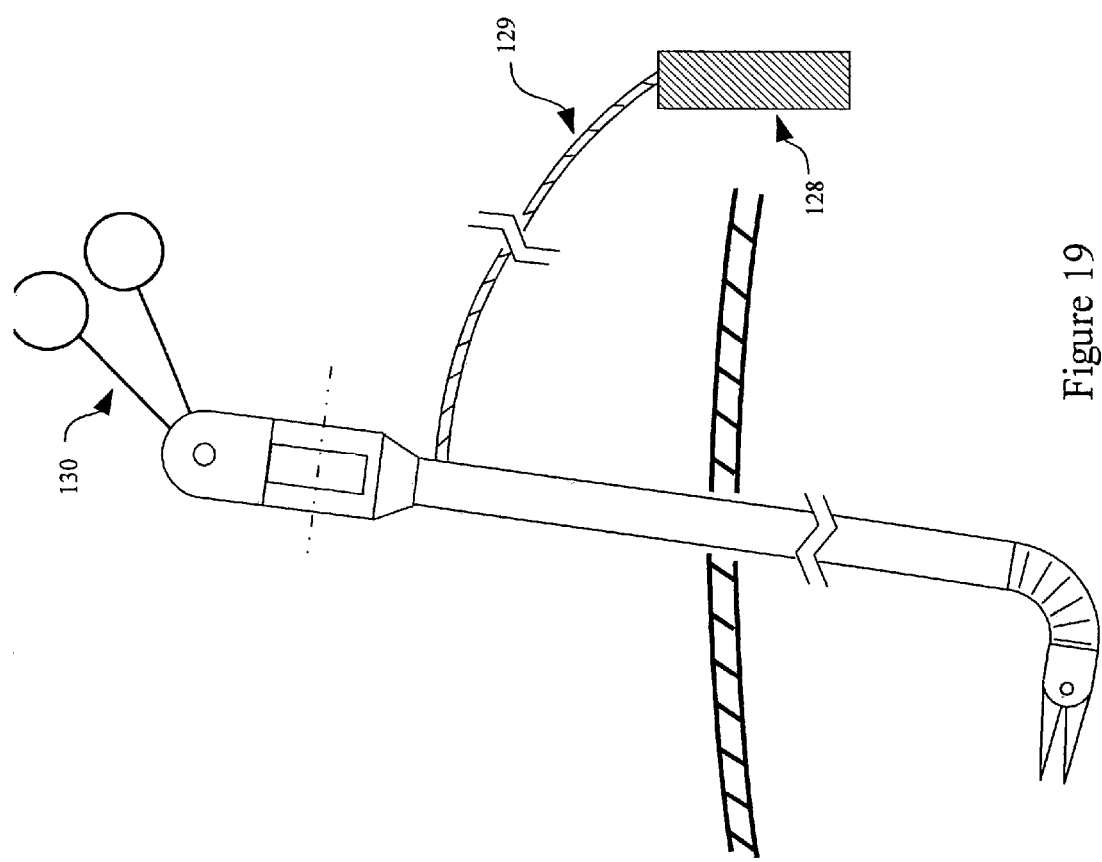
FIG. 19 is a schematic diagram of an alternate embodiment related to FIG. 18 and that illustrates an arrangement where the motors are situated away from the handle via mechanical cables traveling through the flexible conduit.

The motions of the tool and the actuation via the grip can also be controlled by actuators such as electrical motors as shown schematically in FIGS. 18 and 19. In the embodiment shown in FIG. 18, the tool motion control cables 124 and grip actuation rod are driven by electrical motors 125 mounted on the side of the proximal end of the elongated shaft 126, instead of being driven directly by the handle motion member and associated handle. The pitch, yaw and roll motion of the handle is measured by respective rotational sensors such as potentiometers or encoders, and the on-board motion controller (not shown) sends appropriate commands to the motors based on the handle position information. In addition to the features of purely mechanical solutions, this embodiment provides additional benefits such as joint motion scaling, tremor reduction, etc.

As an alternate embodiment, FIG. 19 illustrates an arrangement where the motors 128 are situated away from the handle via the mechanical cables 129 traveling through a flexible conduit. The main benefit of this embodiment is lighter weight and the ability to plug in multiple kinds of instrument to a single bank of motors, thus reducing the cost.

Figure 20:
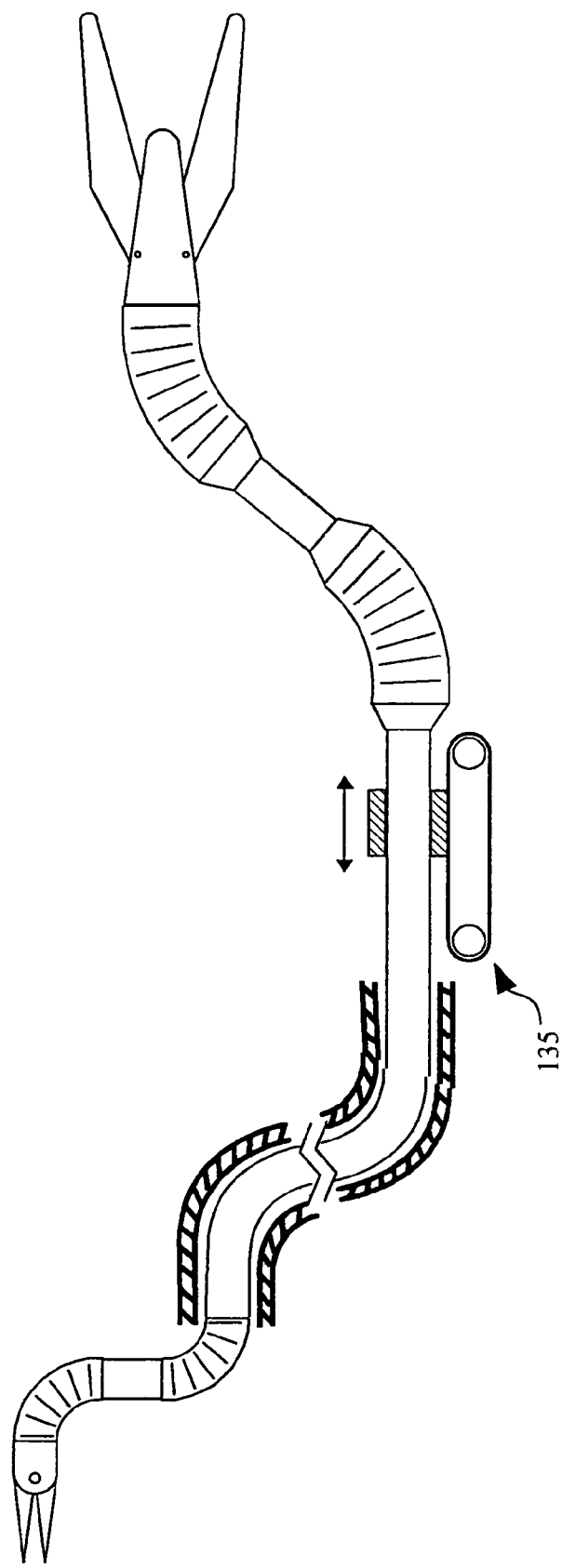
FIG. 20 is a schematic diagram of another embodiment of the invention with multiple motion members, effectuating the forward/backward linear motion by means of a linear actuator to aid the forward/backward motion.

Another potential usage of an actuator is shown in FIG. 20. In embodiments especially with multiple motion members, effectuating the forward/backward linear motion may be difficult as the handle motion members would tend to bend or rotate as well, and in such cases, a linear actuator 130 may be employed to aid the forward/backward motion. Various methods are possible for controlling the linear motion. A simple method could be using an input device such as a toggle switch or button. A somewhat more sophisticated method could be employing a force sensing element mounted on either the elongated shaft or the carriage of the linear actuator to detect the forward/backward force exerted by the surgeon. The force information would then be used by a motion controller to command the linear actuator appropriately.

Figures 21A, 21B, 21C:
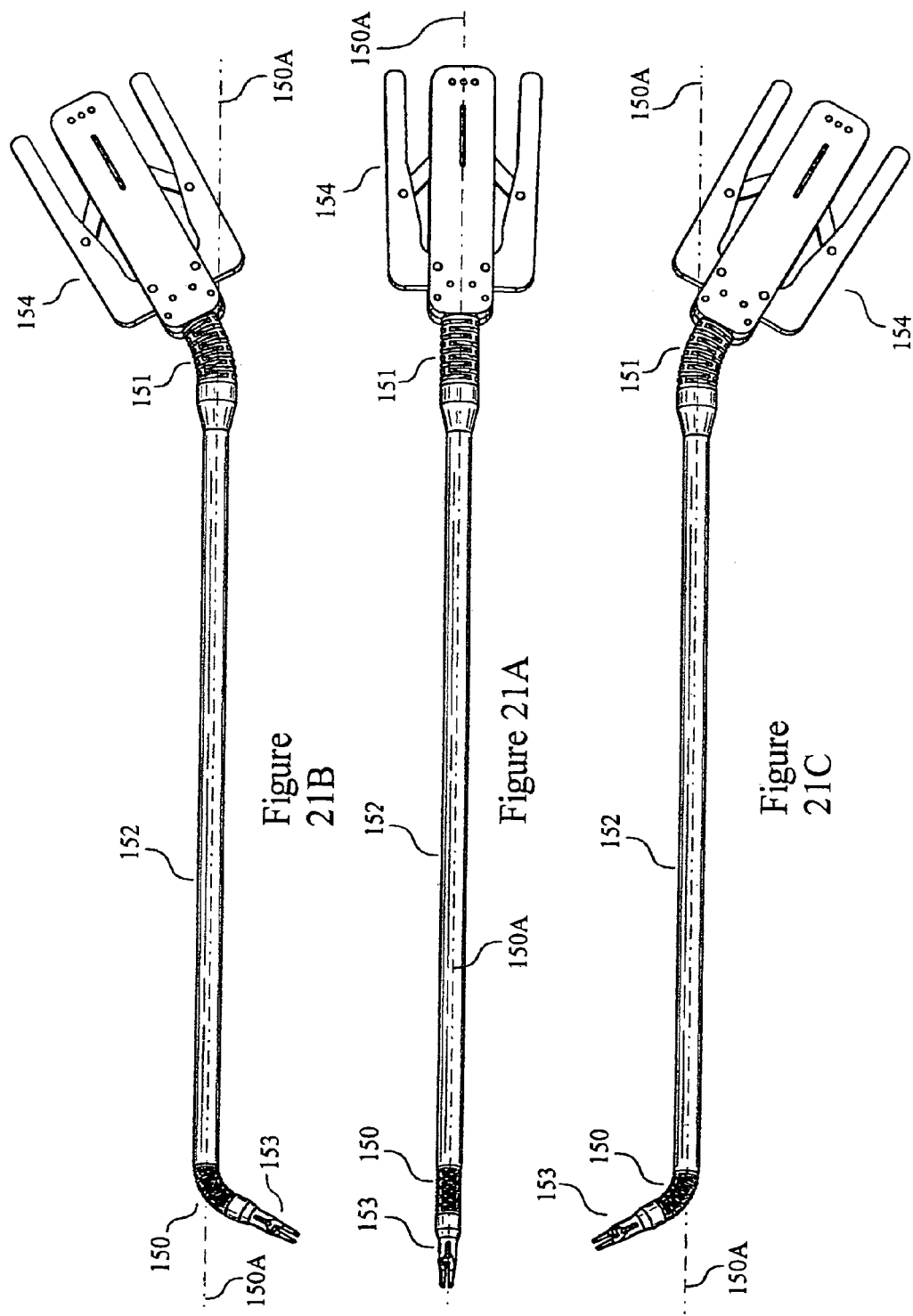
FIGS. 21A, 21B and 21C are separate views showing a more detailed embodiment of the invention in different positions of the handle and tool.

FIGS. 21 through 23 show detailed illustrations of the embodiment as described in FIGS. 1 through 5, where both the tool and the handle motion members 150, 151 are bendable in any direction. The motion members 150 and 151 are connected to each other via cables extending through the elongated rigid shaft 152 in such a way that the tool motion member bends in the opposite direction of the handle motion member, as illustrated in FIG. 21. FIGS. 21A, 21B and 21C are separate views showing the instrument in different positions of the handle and tool. FIG. 21A illustrates the handle and tool in line with each other and in line with the longitudinal axis 150A. FIGS. 21B and 21C illustrate the off-axis motion of the handle and tool. FIG. 21B illustrates the handle 154 bendable upwardly while the corresponding tool bends downwardly relative to axis 150A. FIG. 21C illustrates the handle 154 bendable downwardly while the corresponding tool bends upwardly relative to axis 150A. Of course, in all of the views of FIG. 21 motion can also occur in and out of the plane of the paper (both pitch and yaw).

In FIG. 21, although the end effector 153 in the illustration is a needle holder jaw set, it should be noted that other types of tools may be used. Similarly, although the in-line handle 154 is shown in the illustration, it could be easily substituted by other types of handles as well. Different types of handle could be with or without an opening spring, with or without the finger loops, with or without a lock, with one or two handle bars, or with a pistol-grip instead of an in-line grip, or various combinations thereof.

In FIG. 21 it is noted that the handle motion member 151 is generally of larger diameter than the tool motion member 150. Although this is a preferred arrangement, these diameters may be the same or have various other dimensional relationships therebetween. In the preferred embodiment the bendable sections 150 and 151 are illustrated as being slotted arrangements, however, they may also be of other form such as the bellows structure previously mentioned.

Figure 22A:
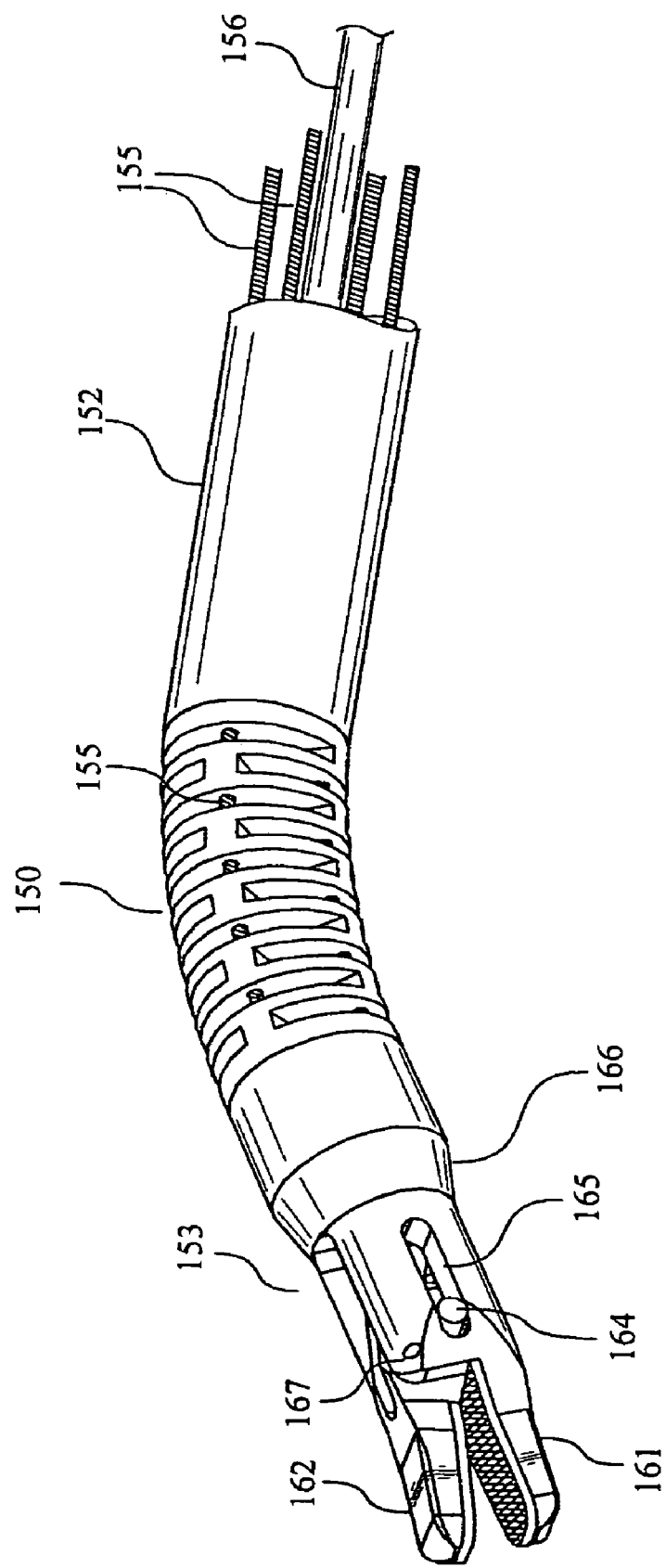
FIG. 22A is a fragmentary perspective view of the tool end of the instrument illustrated in FIG. 21.
Figure 22B:
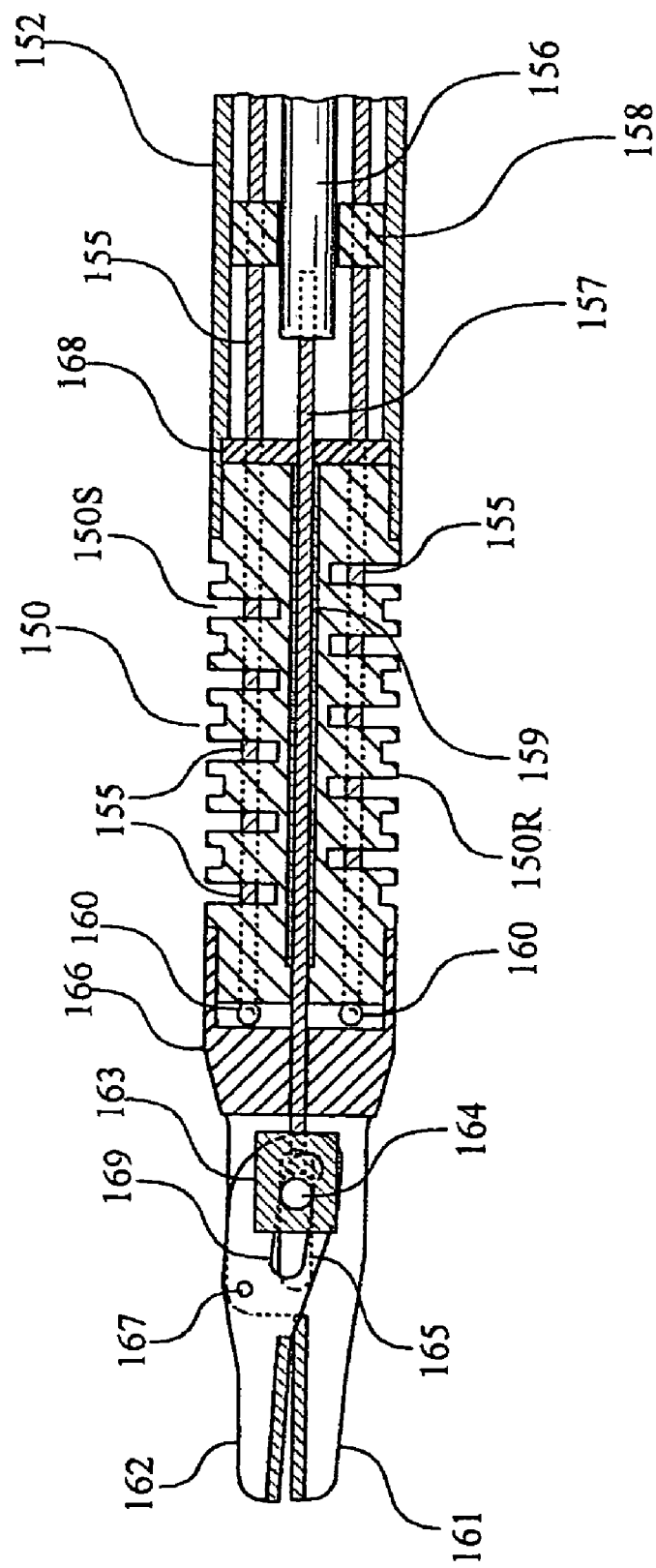
FIG. 22B is a longitudinal cross-sectional view of the tool end of the instrument as illustrated in FIGS. 21 and 22A.
Figure 22C:
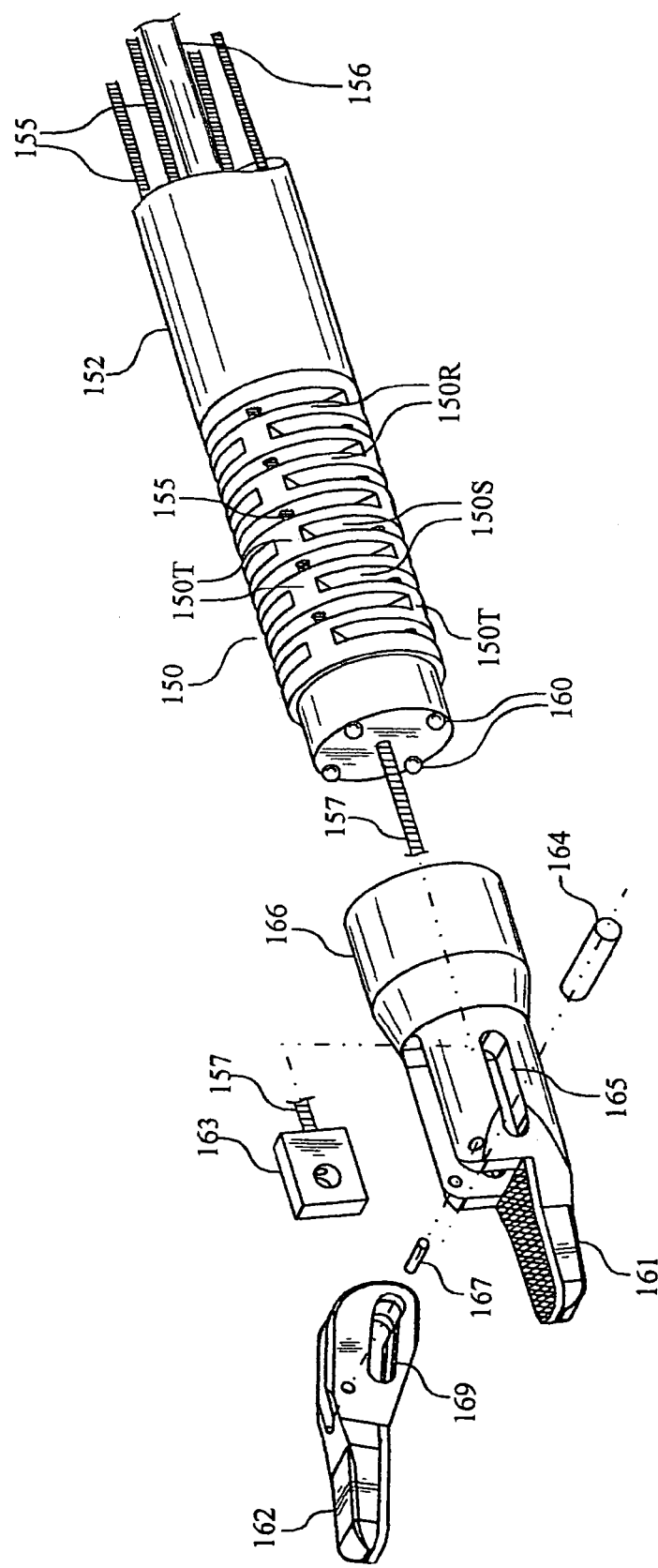
FIG. 22C is an exploded perspective view of the instrument segment illustrated of FIG. 22A.

FIGS. 22A, 22B and 22C further illustrate the tool or end effector 153 and the tool motion member 150 located at the distal end of the elongated rigid shaft 152. FIG. 22A illustrates a perspective view of the tool section where the tool motion member 150 is bent slightly. The bendable motion member 150 and the distal end of the rigid shaft 152 are illustrated as receiving the motion control cables 155 and the tool actuating push rod 156. The tool 153 is firmly fixed on the distal end of the tool motion member 150, and likewise, the proximal end the tool motion member 150 is firmly fixed on the distal end of the rigid shaft 152.

The needle holder (tool 153) has only one jaw that opens in order to increase its grasping force, although the tool could also be provided with both jaws operable. The bottom jaw 161 is part of the jaw yoke 166, and therefore it is not movable with respect to the yoke. The movement of the push rod 156 causes the pin 164 to move along the slot 165 in the yoke 166, and as a result the top jaw 162 moves or pivots about the pin 167.

Reference is now made to the cross-sectional view of the tool section, as illustrated in FIG. 22B. The push rod 156 is flexible at rod 157 in the portion that passes through the tool motion member 150 whereas the portion that is situated inside the rigid shaft 152 is preferably rigid. The flexible push rod 157 is fixedly coupled to the rigid push rod 156. The motion control cables 155 and the rigid push rod 156 are guided by and through the spacer 158 along their paths, and the distal ends of the motion control cables 155 are terminated at 160. The flexible portion of the push rod 157 passes through the center of the tool motion member 150 and the jaw yoke 166, and it terminates by being fixedly coupled to the termination block 163, which in turn carries the pin 164 that traverses along the camming slots 165 (jaw 161) and 169 (jaw 162).

In order to increase the column strength of the tool motion member, a reinforcement thin-walled tube 159 made of stiff material such as PEEK (a polyethylene plastic) is used. The end plate 168 is placed between the tool motion member 150 and shaft 152 to prevent the reinforcement tube 159 from sliding out. It should be noted that depending on the material and geometry of the tool motion member, it may not be necessary to employ such reinforcement tube.

FIG. 22C illustrates an exploded view of the tool section of FIG. 22A. As previously described, the motion control cables 155 are terminated at 160. Forward and backward movement of the rigid push rod 156 moves the termination block 163 and the pin 164 along the slot 165 of the bottom jaw 161. Since the pin 164 also rides in the slot 169 of the top jaw 162, forward and backward motion of the pin 164 respectively opens and closes the top jaw. While the tool actuation rod 156 is disposed at the center of the bendable motion member, the four cables 155 are disposed in a diametric pattern so as to provide the all direction bending.

In FIG. 22C the tool motion member 150 is illustrated as being comprised of a series of ribs 150R that define therebetween a series of slots 150S, that together define alternating direction transverse slots. The ribs 150R extend from a center support that carries the actuation rod 156 and tube 159. The ribs 150R provide a support structure for cables 155. In the particular embodiment described in FIG. 22C between the ribs there is a pattern of staggered ridges 150T disposed at 90 degree intervals about the member. The cables 155 pass through the area of the motion member 150 where these ridges 150T are arranged.

Figure 23A:
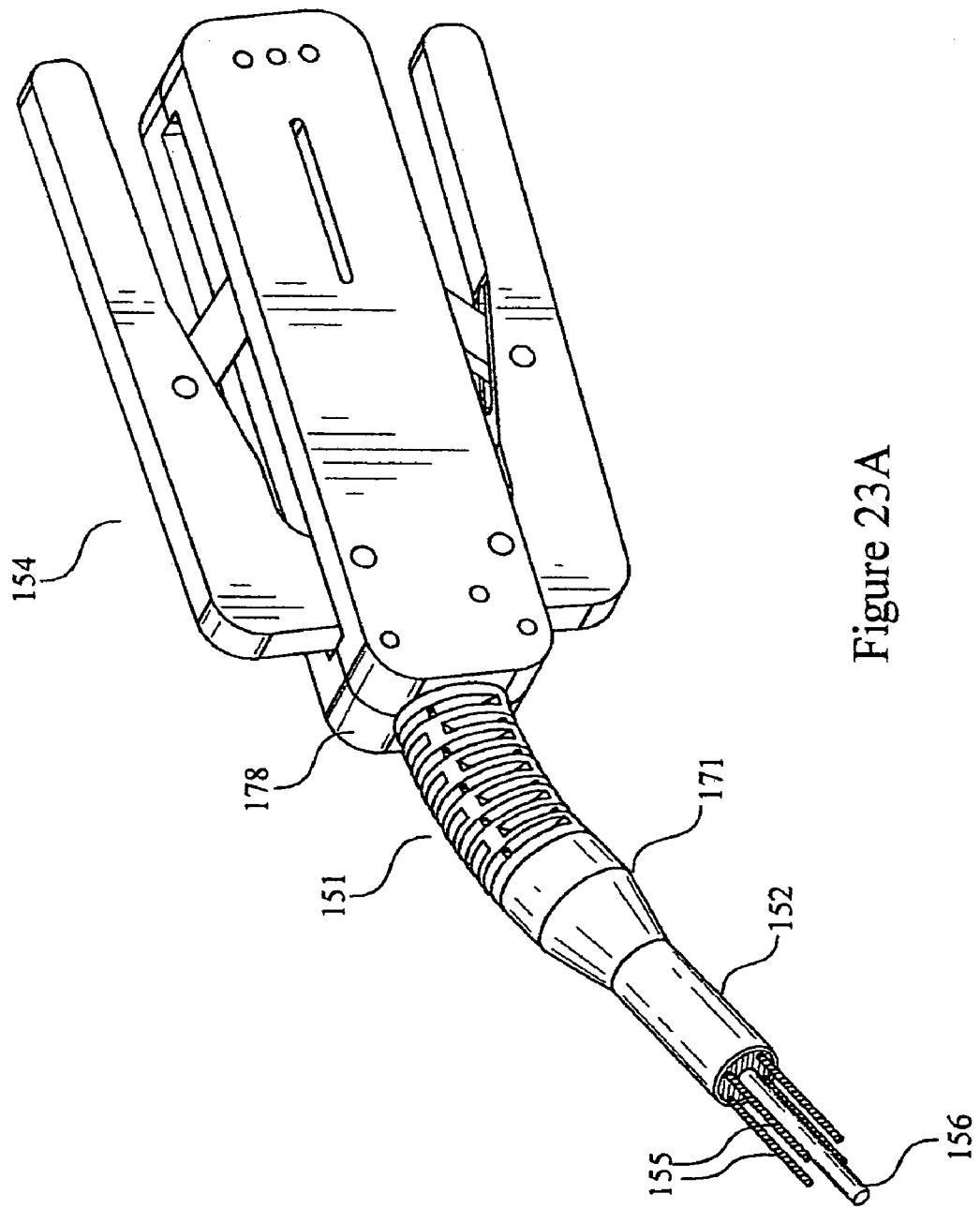
FIG. 23A is a fragmentary perspective view of the handle end of the instrument illustrated in FIG. 21.

FIGS. 23A, 23B, 23C and 23D illustrate in detail the handle section located at the proximal end of the elongated shaft 152. FIG. 23A is a perspective view of the handle section where the handle motion member 151 is slightly bent. In FIG. 23A the same reference characters are used to identify like components previously described in connection with the tool end of the instrument. For example, four motion control cables 155 as well as the tool actuating push rod 156 travel through the handle motion member 151. The cables 155 control bending motion at the tool motion member while rod 156 controls tool actuation. The distal end of the handle motion member 151 is fixedly connected to the proximal end of the elongated shaft 152 via the handle motion member coupler 171, and similarly, the proximal end of the handle motion member 151 is fixedly mounted to the handle body 178 of handle 154.

Figure 23B:
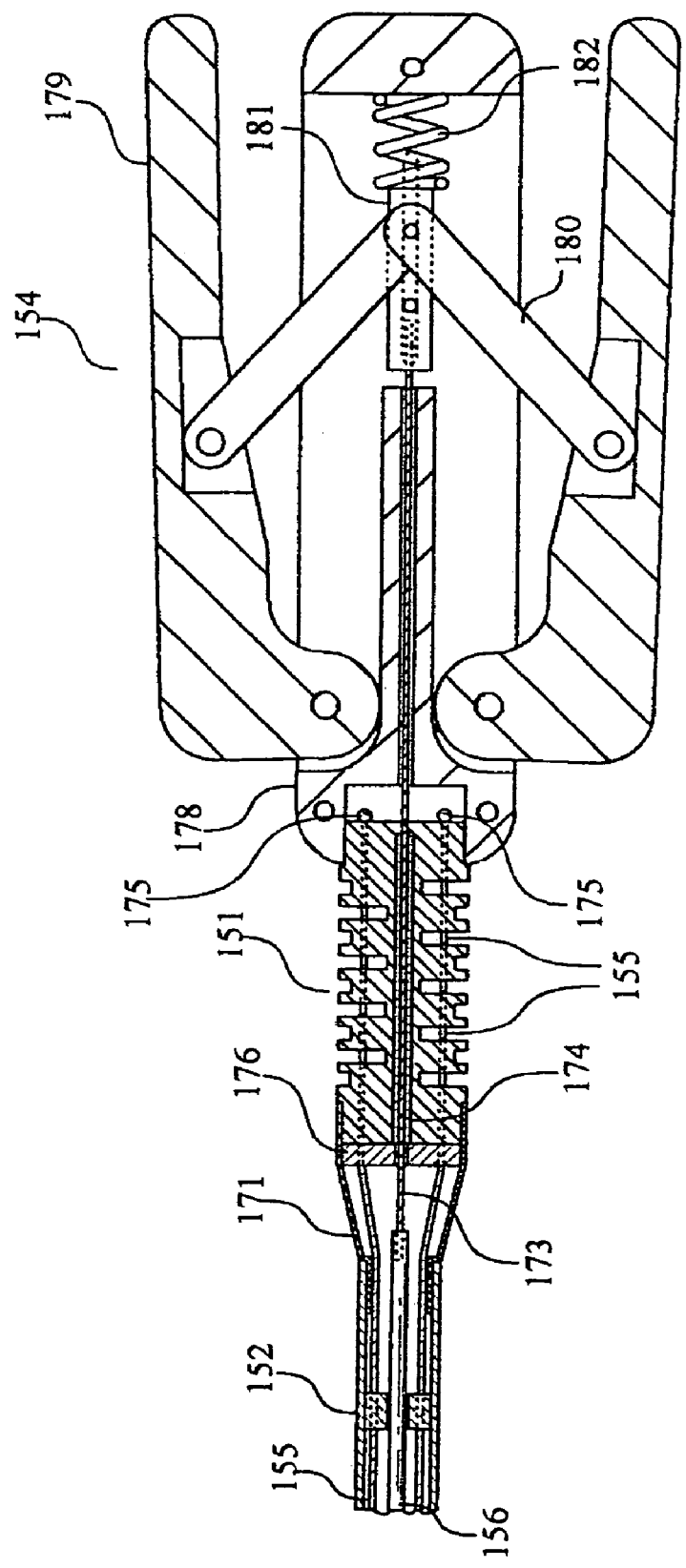
FIG. 23B is a longitudinal cross-sectional view of the handle end of the instrument as illustrated in FIGS. 21 and 23A.

Reference is now made to the cross-section view of the handle section, as illustrated in FIG. 23B. As with the tool section, the tool actuating push rod 156 is flexible (flexible rod portion 173) in the portion that passes through the handle motion member 151 whereas the portion that is situated inside the rigid shaft 152 is preferably rigid. The flexible portion 173 is fixedly coupled to the rigid push rod 156. The motion control cables 155 travel through the outer edge of the handle motion member 151 and are terminated at 175. The four cables. 155 are disposed in the same pattern as discussed previously regarding the tool section (see FIG. 22C). The flexible push rod 173 travels through the center of the handle motion member 151 and is terminated at the sliding block 181. Similarly to the tool motion member, a thin-walled reinforcement tube 174 is placed at the center lumen of the handle motion member 151 to increase the column strength of the handle motion member. An end plate 176 is placed between the coupler 171 and the handle motion member 151 to prevent the reinforcement tube 174 from sliding out. Depending on the material and geometry of the handle motion member, the reinforcement tube may not be necessary. Opening and closing of the handle bars 179 causes forward and backward movement of the sliding block 181 via the handle links 180, which in turn, via the rods 156, 157 and 173, causes the jaw to respectively open and close. The handle spring 182 biases the handle to be open normally which is typical of needle holders. For other types of jaws, it may not be desirable to have the bias spring.

Figure 23C:
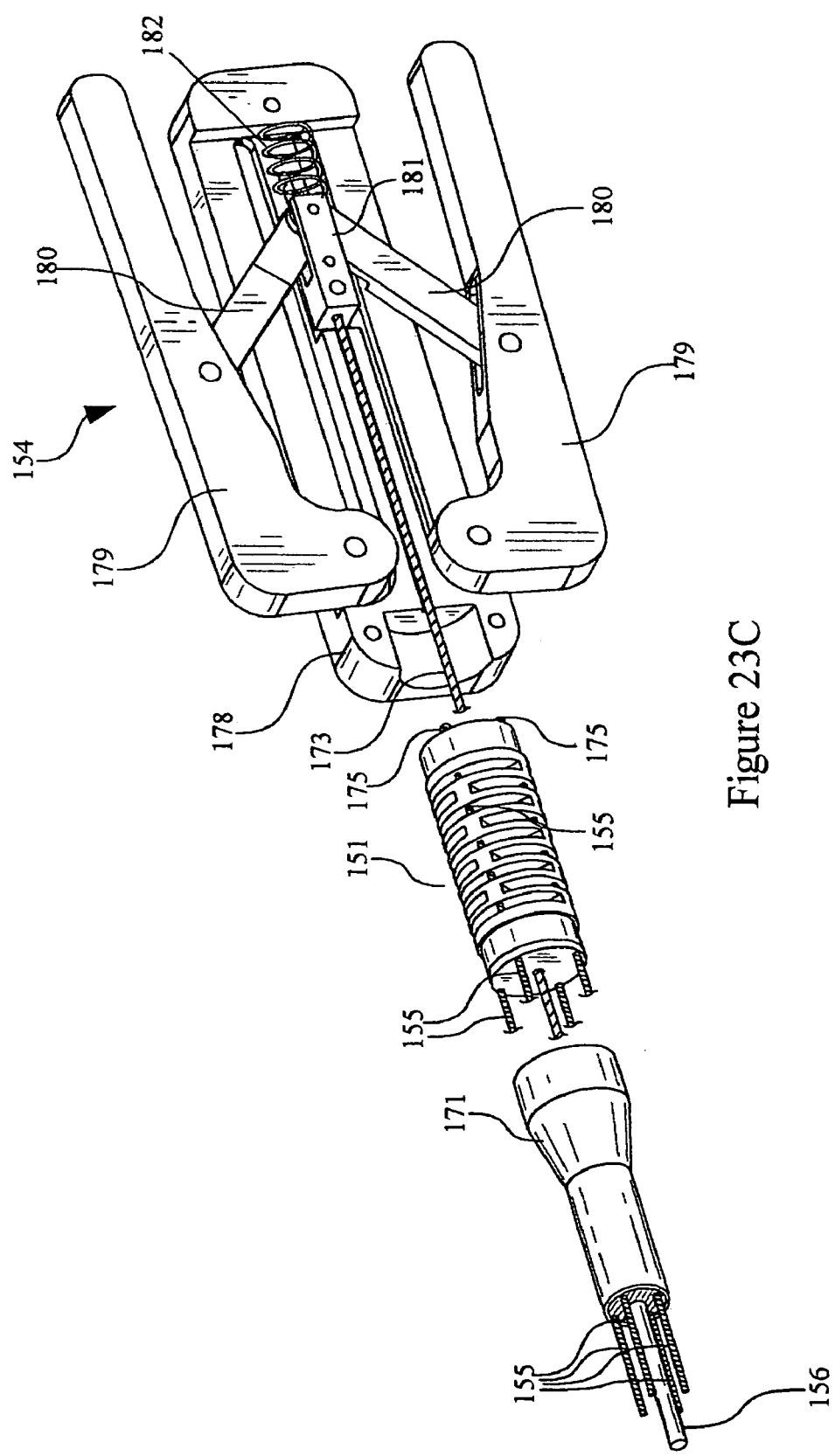
FIG. 23C is an exploded perspective view of the instrument segment illustrated of FIG. 23A.
Figure 23D:
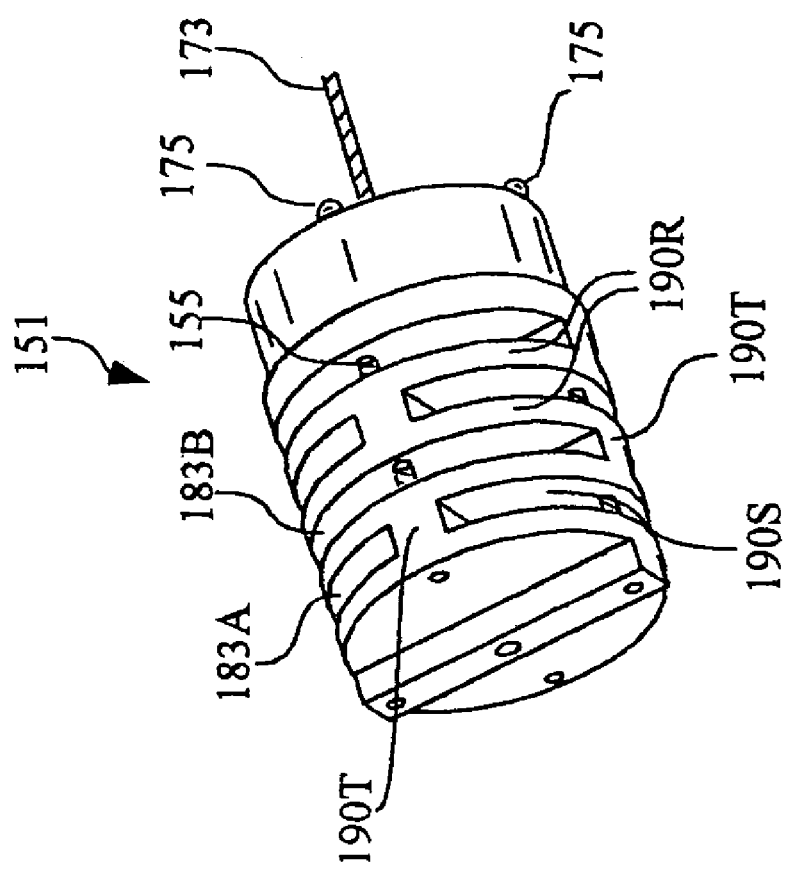
FIG. 23D is a cutaway perspective view of the bendable section of the instrument at the handle end.

FIG. 23C further illustrates the handle section of the instrument. Note that the motion control cables 155 are situated on the outer edge of the handle motion member 151 and are terminated at 175, whereas the flexible push rod 173 passes through the handle motion member 151 at its center and terminates at the sliding block 181. The geometry of the handle motion member 151 in this embodiment is further illustrated in the cutaway view of the handle motion member, as shown in FIG. 23D. As discussed previously, the bendable tool and handle motion members can be constructed in many different embodiments such as a ribbed or bellowed construction. FIG. 23D illustrates the preferred embodiment of the handle motion member 151. Substantially the same construction is shown herein for the tool motion member 150.

In FIG. 23D the bendable motion section is illustrated as having alternating slots 183A and 183B extending in transverse directions for allowing the motion member to bend in any direction while maintaining a continuous center region for high column strength. FIG. 23D illustrates the motion member as being comprised of a series of ribs 190R that define therebetween a series of slots 190S. The ribs 190R extend from a center support that carries the actuation rod 173 and tube 174. The ribs 190R provide a support structure for cables 155. In the particular embodiment described in FIG. 23D between the ribs there is a pattern of staggered ridges 190T that define the alternating slots and that are disposed at alternating 90 degree intervals about the member. The cables 155 pass through the area of the motion member 151 where these ridges 190T are.

Reference has been made to the manner in which the instrument shown in FIGS. 21-23 can be manipulated to perform a surgical task. For example, FIG. 21 shows different positions of the instrument. These possible movements are brought about by the surgeon grasping the handle and bending or turning the handle virtually in any direction. For example, and in connection with FIG. 21C, the handle is illustrated as turned or tilted down with a corresponding turning or tilting of the tool section in an upward direction. In addition, by rotating the handle about the shaft the surgeon can tilt or turn the handle in and out of the plane depicted in FIG. 21C. Depending upon the direction of manipulation by the surgeon, the control cable 155 that is disposed closest in line to the direction of turning is loosened or slackened, and the opposite cable 155 is tightened. This action causes the opposite direction turning as depicted in FIG. 21. Essentially the tightened cable pulls the tool end in the opposite direction. By providing the four cable quadrant array of cables handle-to-tool action is in any direction.

Figure 24:
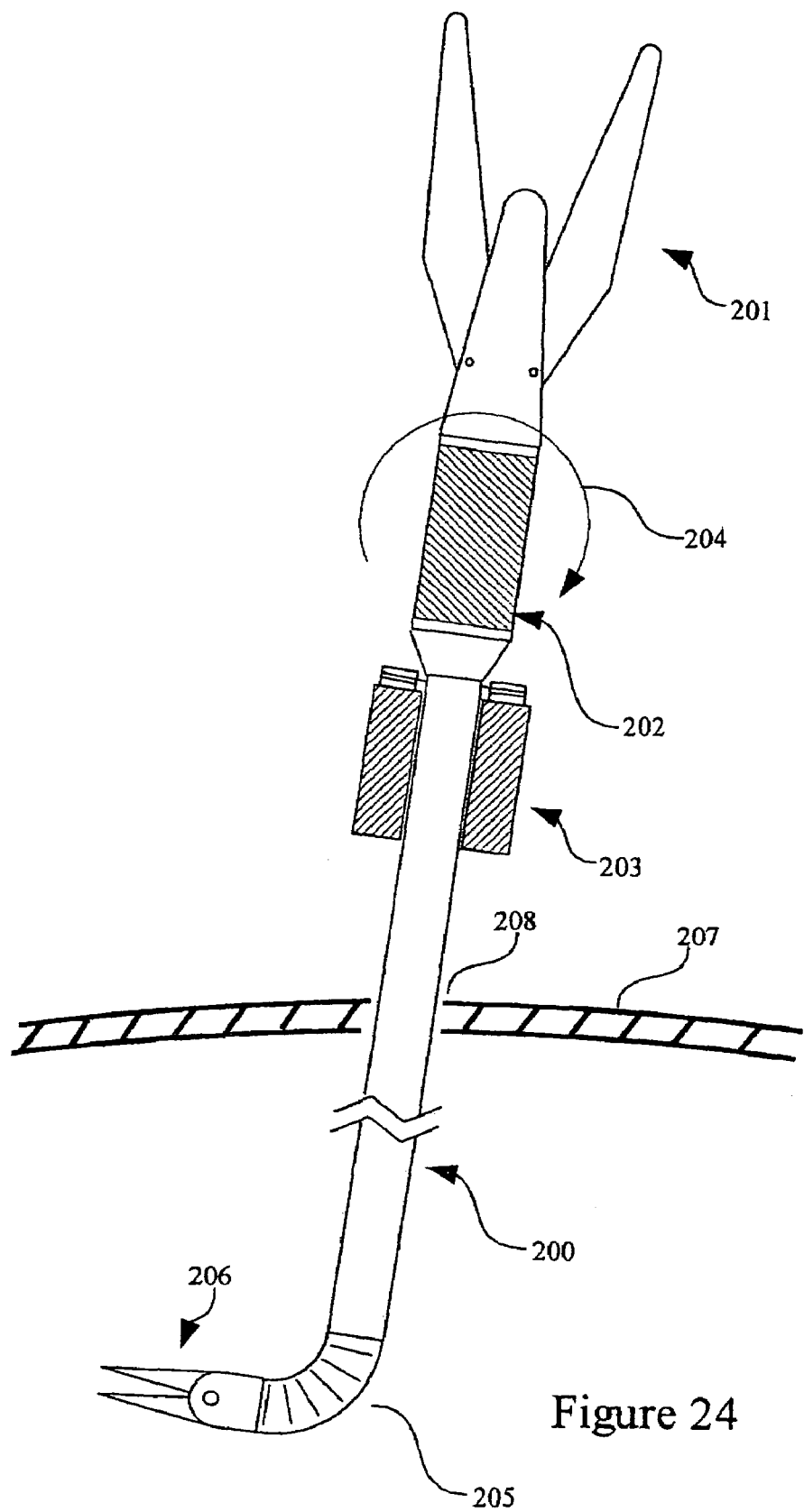
FIG. 24 illustrates another embodiment of the present invention where the movement of the tool motion member is controlled by the torque applied at the handle motion member.

Another embodiment of the present invention is illustrated in FIG. 24 showing the instrument passing through an anatomic wall 207 at aperture 208. In this embodiment the movement of the tool motion member 205 is controlled by the torque applied at the handle motion member 202 rather than the movement of the member itself. Due to the fulcrum effect as well as usage of long elongated instruments, the surgeon often has to move the instrument handle in a wide range of motion during a particular medical procedure in order to perform the surgical task at the intended target area. As a result, the surgeon is often forced into very awkward postures, and manipulating the instrument handle further to control the tool motion member in those circumstances can be extremely difficult.

In the embodiment of FIG. 24, the handle 201 is disposed at the proximal end of the elongated shaft 200 via the torque sensing member 202 which continuously measures the torque applied by the surgeon, as illustrated by the rotational torque arrow 204. Based on the torque measurement, the on-board motion controller (not shown) sends appropriate commands to the motors 203 for controlling the tool motion member 205. The torque sensing member 202 is preferably relatively stiff such that the movement of the handle 201 with respect to the elongated shaft 200 is minimal for reasons described above (to enhance surgeon manipulation). Tool actuation may be driven manually by the handle 201 itself as in FIG. 4 or it could be driven electronically by the motor as in FIG. 18. The motors could also be placed remotely as in FIG. 19.

In the embodiment of FIG. 24 the handle end of the instrument is manipulated in substantially the same way as in earlier embodiments that have been described herein. FIG. 24 shows by arrow 204 the direction of motion at the handle end of the instrument, and the corresponding position of the tool 206, bent to the left in FIG. 24. In FIG. 24, instead of the motion member 205 being directly cable driven from the handle member, it is driven by cabling that couples from the control motors 203, which is in turn controlled from the torque sensing member 202. A full range of motion can be obtained from the instrument shown in FIG. 24 in all directions, as in earlier embodiments described herein.

Figure 25:
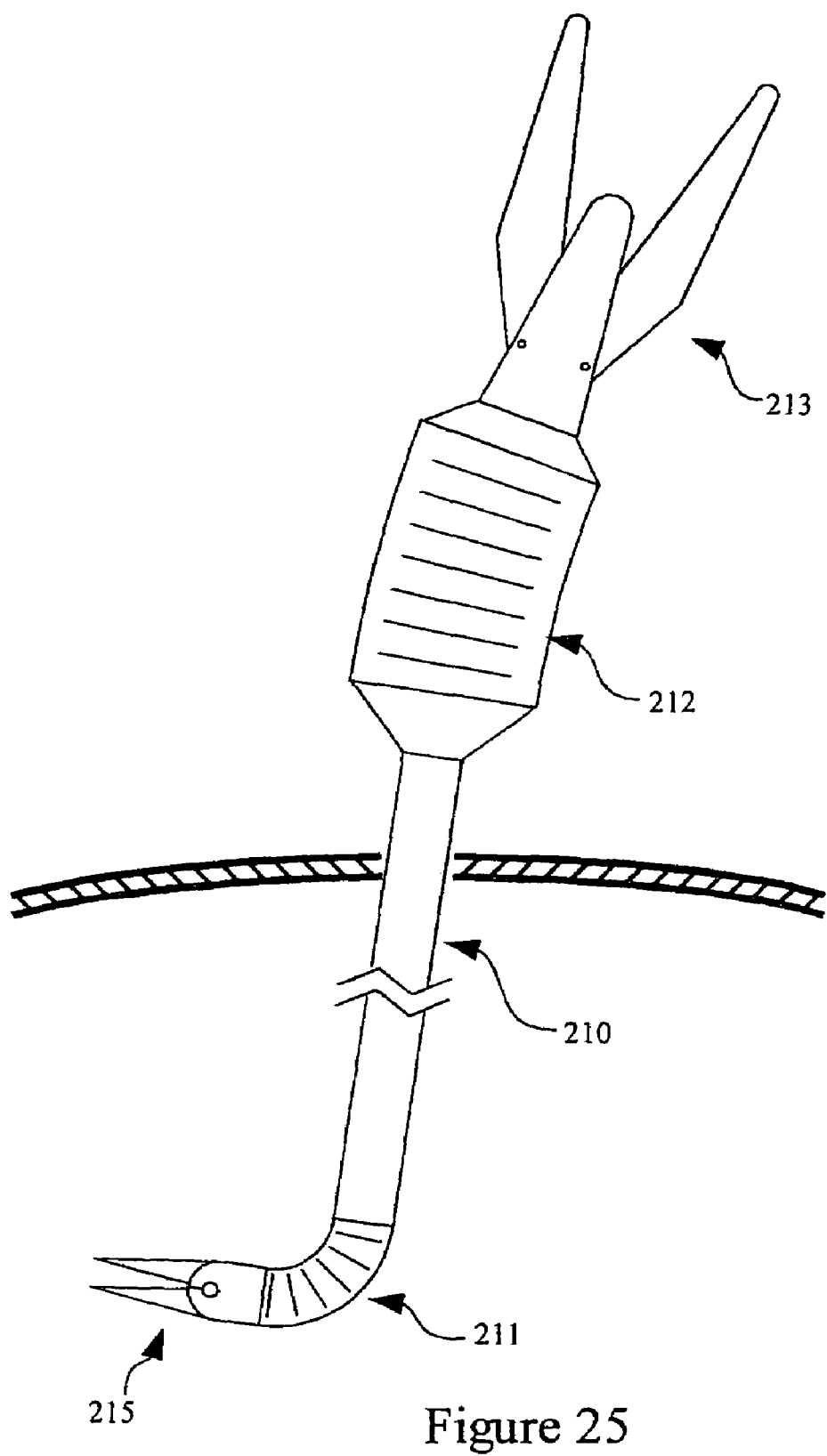
FIG. 25 is still a further embodiment of the present invention relating to FIG. 24.

In the embodiment shown in FIG. 25, the benefit of the previous embodiment shown in FIG. 24 is, in essence, combined with the simplicity of the embodiment shown in FIGS. 1-4. As in the embodiment of FIGS. 1-4, the tool motion member 211 that couples to the tool 215 is disposed at the distal end of the instrument shaft 210. The handle 213 is disposed at the proximal end of the instrument. The handle 213 couples to the shaft 210 via the handle motion member 212, and both motion members 211 and 212 are bendable in any direction. In addition to what is illustrated in FIGS. 1-4, however, the embodiment in FIG. 25 simulates the effect of torque sensing member 202 of FIG. 24 by using a handle motion member 212 that is much larger in diameter and laterally stiffer than that of the tool motion member 211. Due to large diameter ratio between the motion members 211 and 212, small bending of the handle motion member 212 causes a substantial bending of the tool motion member 211. At the same time, because the handle motion member 212 is substantially stiff laterally, the surgeon operating the tool has to apply a reasonable amount of torque to the handle to cause the desired movement at the tool motion member. Without such lateral stiffness at the handle motion member, the tool motion member may bend too freely and may thus be difficult to control.

Figure 26:
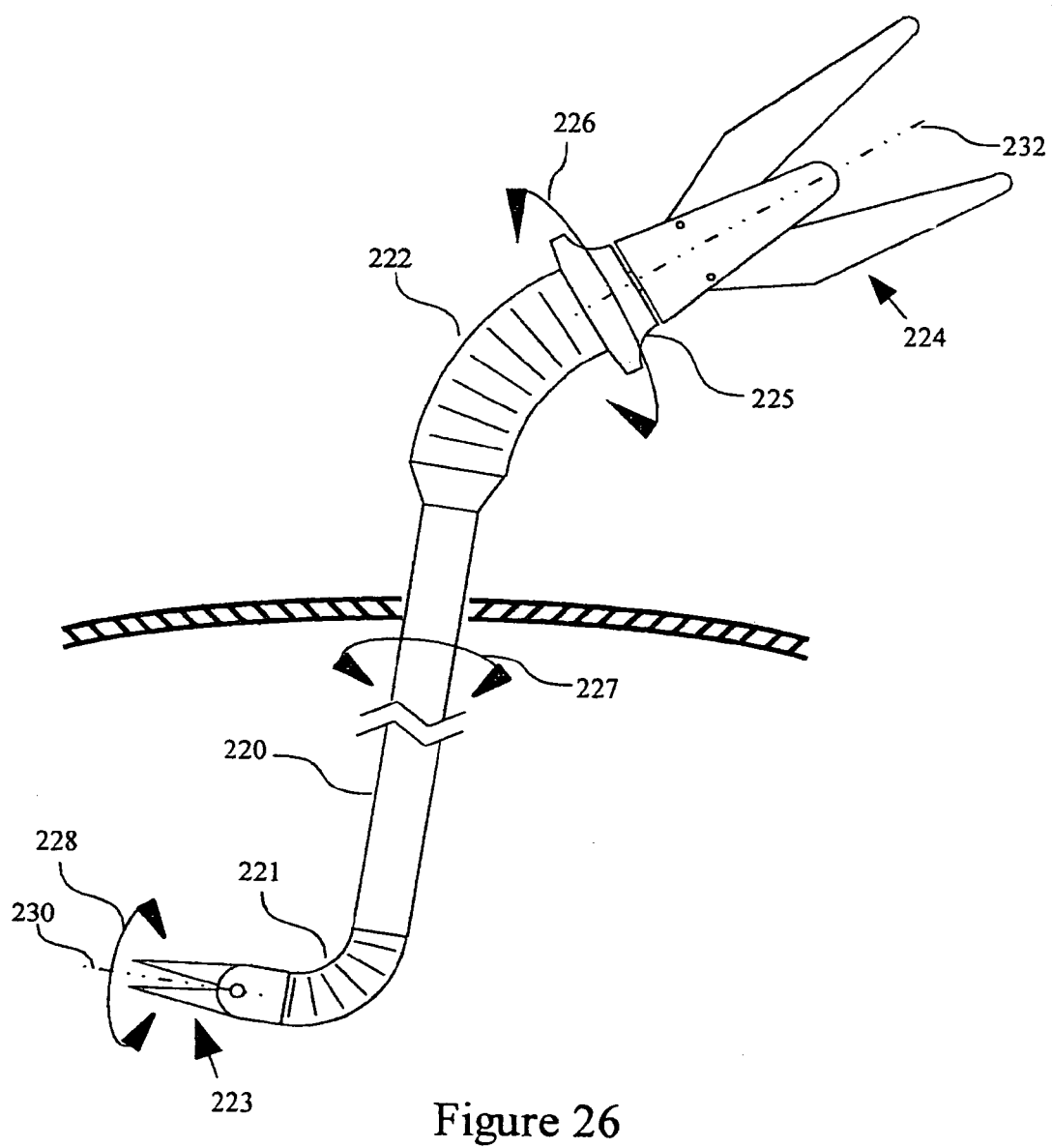
FIG. 26 is a further embodiment of the present invention where ease of use of the instrument is further enhanced by making it simpler to roll the tool end about its axis, an essential motion in suturing at off-axis angle.

Still another embodiment of the present invention is illustrated in FIG. 26 where ease of use of the instrument is further enhanced by making it simpler to roll the tool end about its axis 230, an important motion in suturing at an off-axis angle. Similar to the embodiment of FIGS. 1-4, FIG. 26 shows an instrument with an instrument shaft 220 and with the tool 223 and the handle 224 disposed respectively at the distal and proximal ends of the shaft 220, via motion members 221 and 222. However, unlike the embodiment of FIGS. 1-4, in this embodiment, the handle motion member 222 has a rolling-motion wheel 225 fixedly mounted at its proximal end, which is able to axially rotate about axis 232 and relative to the handle 224 as shown by the double-headed arrow 226. This action causes a corresponding rotation of the tool 223 about axis 230 and as illustrated by the double-headed arrow 228. Therefore, the surgeon operating the instrument can roll the instrument tool 223 simply by rolling the rolling-motion wheel 225 with his or her thumb rather than rolling the whole handle 224.

Figure 27:
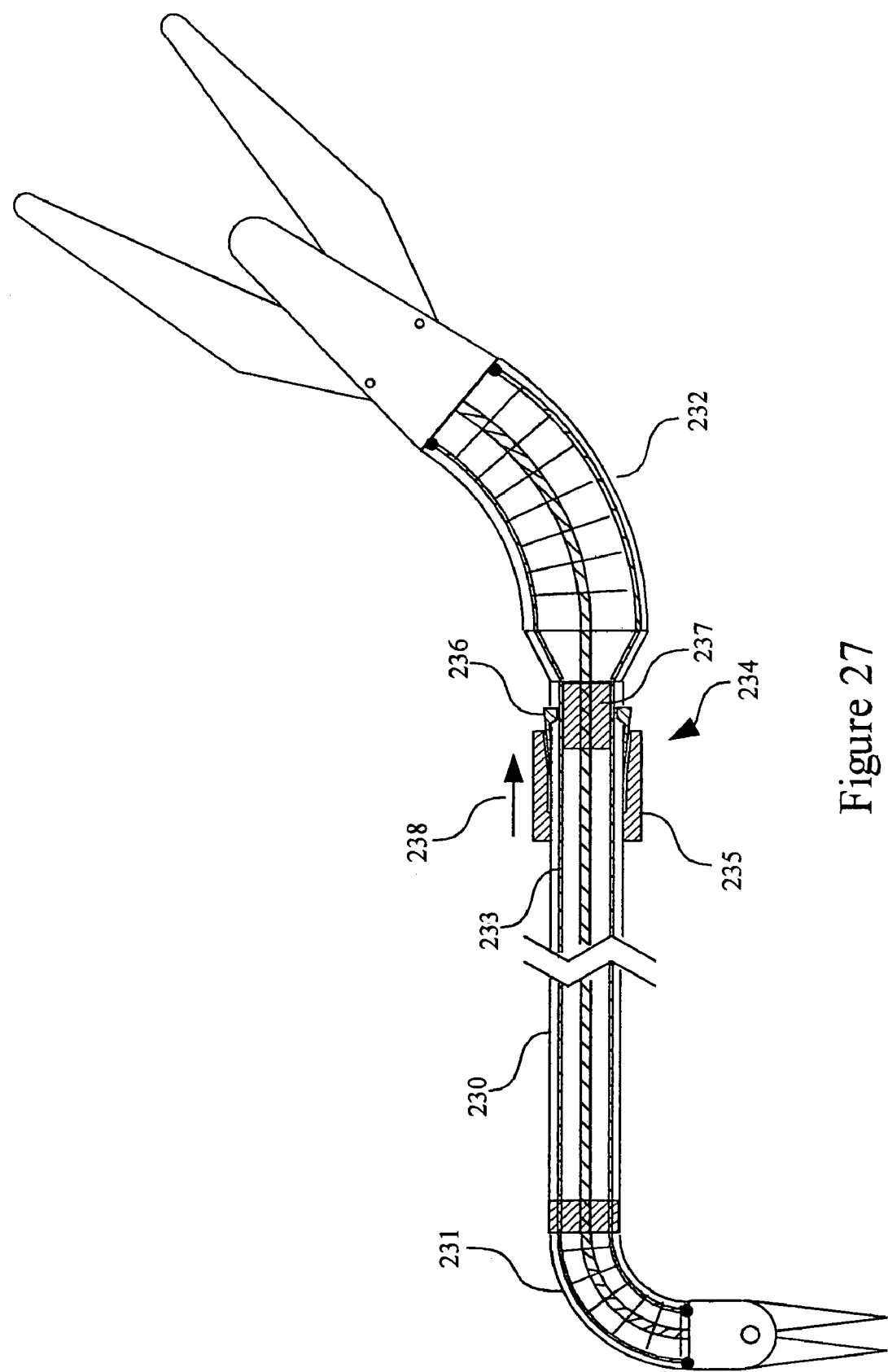
FIG. 27 illustrates still another embodiment of the present invention.

Yet another embodiment of the present invention that further enhances ease of use is illustrated in FIG. 27. In addition to the embodiment of FIGS. 1-4, FIG. 27 also illustrates the motion member locking mechanism 234. While performing the surgical procedure, the surgeon operating the instrument may desire to lock the orientations of the bendable motion members temporarily so that he or she would not need to continuously exert torque at the handle motion member in order to maintain the desired orientation. The motion member locking mechanism 234 may consist of the locking collar 235, the locking wedge 236 and the cable guide 237. When the surgeon desires to lock the orientation of the motion member, he or she simply slides the locking collar 235 in the direction shown by the arrow 238, which then presses down the locking wedge 236 against the cable guide 237 with the control cables 233 pinched in between. Once pinched, the control cables 233 would not be able to move, and as a result, the orientations of the motion members 231 and 232 will be fixed. The motion member orientation lock can be released by sliding the locking collar 235 backward toward the instrument tip.

There are several improvements brought forth by employing bendable sections for the motion members as opposed to other mechanisms such as pivotal joints or ball-and-socket joints.

A first important attribute of a bendable member is in its inherent lateral (bending) stiffness, especially when used for the proximal handle motion member. In a jointed arrangement the proximal joint is situated between the elongated shaft and the control handle, together with the fulcrum at the incision. This behaves as a "double-joint" and the instrument may have a serious tool stability issue if the joint is "free" to move. Suppose the operating surgeon slightly moves his/her wrist while holding the control handle of the instrument. If the joint is "free" to move without providing substantial support resistance, due to the fulcrum effect of the long elongated shaft passing through the incision, it will result in substantial, unintended swinging of the tool end of the instrument in opposite direction. In a typical laparoscopic or endoscopic procedures where the operating field is small, such instability of the tool will render the tool potentially dangerous and unusable. Unlike the pivotal or ball-and-socket joints that are "free" to move, a bendable member has inherent stiffness which acts to provide necessary support for stabilizing the operator hand's wrist movement, which in turn stabilizes the tool motion. By varying the material and geometry of the bendable member, the appropriate level of stability could be selected.

A second important attribute of the bendable member, especially for bending in two degrees of freedom, is its uniformity in bending. Because the bendable member can bend in any direction uniformly, it has no inherent singularity, and as the result, the operator can produce uniform rolling motion of the tool, an important motion for tasks such as suturing, simply by rolling the control handle. On the other hand, if the motion members are comprised of series of pivotal joints, not only may it bind due to singularities, but the rolling of the control handle will result in unwanted side motion of the tool as well, affecting its usability for surgical procedure.

A third attribute of the bendable member is its ability to transmit substantial torque axially. By selecting appropriate material and geometry, the bendable member can be constructed to transmit torque axially necessary to perform surgical procedure. On the other hand, the motion member comprised of ball-and-socket joints will not be able to transmit thye necessary torque from the handle to the tool end.

A fourth attribute of the bendable member is that it has no sharp bending point, location or pivot and thus this results in an increased life and higher performance. Either pivotal or ball-and-socket joints on the other hand have sharp corners which can increase friction, reduce life and decrease performance of the tool actuation push rod passing through.

A fifth attribute of the bendable member is in the reduction of manufacturing cost. The bendable motion member can be injection molded as a single body, thus significantly reducing the cost. Pivotal or ball-and-socket joints are comprised of more part and this results in a higher manufacturing cost.

Lastly, a sixth attribute of the bendable member is that it can be easily customized. By varying the stiffness at different points of the bendable member, one can optimize its bending shape for specific applications.

While this invention has been particularly shown and described with references to preferred embodiments thereof, it will be understood by those skilled in the art that various changes in form and details may be made therein without departing from the scope of the invention encompassed by the appended claims. For example, the embodiments described herein have primarily used four control cables for providing all direction motion of the motion members. In alternate embodiments fewer or greater numbers of cables may be provided. In a most simplified version only two cables are used to provide single DOF action at the bendable motion member.

What is claimed is:

1. A surgical instrument comprising:
an elongated instrument shaft having proximal and distal ends;
a tool disposed from the distal end of the instrument shaft;
a control handle disposed from the proximal end of the instrument shaft;
a distal motion member for coupling the distal end of said elongated instrument shaft to said tool;
a proximal bendable member that is bendable into a curved configuration for coupling the proximal end of said elongated instrument shaft to said handle;
actuation means extending between said distal motion member and said proximal bendable member for coupling motion of said proximal bendable member to said distal motion member for controlling the positioning of said tool; and a rolling-motion wheel adjacent the control handle and rotatable relative to the control handle for causing a corresponding rotation of the tool about a distal tool roll axis.

2. The surgical instrument of claim 1 wherein said distal motion member comprises a distal bendable member and said actuation means comprises cabling that couples between said proximal and distal bendable members, whereby manipulation of said proximal bendable member from said handle controls bending of said distal bendable member via said cabling.

3. The surgical instrument of claim 2 wherein said proximal bendable member has a diameter that is different than the diameter of said distal bendable member.

4. The surgical instrument of claim 2 including a mechanism for locking the relative orientation between the proximal and distal bendable members at a predetermined position by means of a cable restraining device that holds the cables in a pre-selected state.

5. The surgical instrument of claim 1 including a distal axial rotation joint for axially rotating at least one of the distal motion member and tool relative to the instrument shaft.

6. The surgical instrument of claim 1 wherein said proximal bendable member comprises a flexible unitary multi-slotted structure including multiple discs that define multiple slots that are separate and non-contiguous.

7. The surgical instrument of claim 1 wherein the control handle is able to axially rotate relative to at least one of the instrument shaft and proximal bendable member.

8. The surgical instrument of claim 1 further including another proximal bendable member and another distal motion member for multi-modal controlled movement of the tool.

9. The surgical instrument of claim 8 wherein said instrument shaft is inherently flexible for passage intraluminally.

10. A medical instrument comprising:
an instrument shaft having proximal and distal ends;
a working member disposed from the distal end of the instrument shaft; and
a control handle disposed from the proximal end of the instrument shaft;
said working member being coupled to the distal end of said instrument shaft via a first movable member;
said control handle coupled to the proximal end of said instrument shaft via a second movable member;
whereby movement of said control handle with respect to said instrument shaft via said second movable member causes attendant movement of said working member with respect to said instrument shaft via said first movable member;
wherein both of the movable members comprise a bendable motion member, each bendable motion member providing at least one degree of freedom and the bending stiffness of the second movable member being different from the bending stiffness of the first movable member.

11. The medical instrument of claim 10 wherein the bending stiffness of the second bendable member is greater than the bending stiffness of the first bendable member.

12. The medical instrument of claim 10 wherein the maximum transverse cross-sectional dimension of the second movable member is different than that of the first movable member.

13. The medical instrument of claim 10 wherein the diameter of the second bendable member is greater than the diameter of the first bendable member.

14. The medical instrument of claim 10 wherein at least one of said first and second bendable motion members includes a plurality of separately disposed slots extending transverse to the longitudinal axis of the bendable motion member to enable lateral bending thereof.

15. The medical instrument of claim 14 wherein each said bendable motion member comprises a unitary non-jointed bendable member.

16. The surgical instrument of claim 10 wherein the control handle is able to axially rotate relative to at least one of the instrument shaft and second movable member.

17. The surgical instrument of claim 10 including a mechanism for locking the relative orientation between the first and second movable members at a predetermined position.

18. The surgical instrument of claim 10 including a distal axial rotation joint for axially rotating at least one of the second bendable member and tool relative to the instrument shaft.

19. The surgical instrument of claim 10 including a rolling-motion wheel adjacent the control handle and rotatable relative to the control handle for causing a corresponding rotation of the working member about a distal roll axis.

20. A surgical instrument comprising:
an elongated instrument shaft having proximal and distal ends;
a tool disposed from the distal end of the instrument shaft; and
a control handle disposed from the proximal end of the instrument shaft;
said tool being coupled to the distal end of said elongated instrument shaft via a distal movable member;
said control handle coupled to the proximal end of said elongated instrument shaft via a proximal movable member;
whereby movement of said control handle with respect to said elongated instrument shaft via said proximal movable member causes attendant movement of said tool with respect to said elongated instrument shaft via said distal movable member;
wherein the maximum transverse cross-sectional dimension of the second movable member is different than that of the first movable member;
further including another proximal movable member and another distal movable member for multi-modal controlled movement of the tool.

21. The surgical instrument of claim 20 wherein both movable members are bendable members, and the diameter of the proximal bendable member is different than the diameter of the distal bendable member.

22. The surgical instrument of claim 21 wherein the diameter and bending stiffness of the proximal bendable member is greater than the diameter and bending stiffness of the distal bendable member.

23. The surgical instrument of claim 20 further including a rolling-motion wheel adjacent the control handle and rotatable relative to the control handle for causing a corresponding rotation of the tool about a distal tool roll axis.

24. The surgical instrument of claim 20 wherein the control handle is able to axially rotate relative to at least one of the instrument shaft and proximal movable member.

25. The surgical instrument of claim 20 including a mechanism for locking the relative orientation between the distal and proximal movable members at a predetermined position.

26. The surgical instrument of claim 20 further including distal and proximal axial rotation joints wherein the proximal axial rotation joint actuates the distal axial rotation joint.

27. The surgical instrument of claim 20 including a distal axial rotation joint for axially rotating at least one of the distal movable member and tool relative to the instrument shaft.

28. The surgical instrument of claim 20 wherein said proximal movable member comprises a bendable member and said distal movable member comprises a pivotal joint.

29. An instrument comprising:
an instrument shaft having proximal and distal ends;
a working member disposed from the distal end of the instrument shaft; and
a control handle disposed from the proximal end of the instrument shaft;
said working member being coupled to the distal end of said instrument shaft via a distal movable member;
said control handle coupled to the proximal end of said instrument shaft via a proximal movable member;
whereby movement of said control handle with respect to said instrument shaft via said proximal movable member causes attendant movement of said working member with respect to said instrument shaft via said distal movable member;
wherein the proximal movable member is able to axially rotate relative to the control handle;
and further including a rolling-motion wheel adjacent the control handle and rotatable relative to the control handle for causing a corresponding rotation of the tool about a distal tool roll axis.

30. The instrument of claim 29 wherein the distal movable member is able to axially rotate relative to the working member.

31. The instrument of claim 29 further including distal and proximal axial rotation joints wherein the proximal axial rotation joint actuates the distal axial rotation joint.

32. The surgical instrument of claim 29 wherein both movable members are bendable members, and the maximum transverse cross-sectional dimension of the second bendable member is different than that of the first bendable member.

33. The surgical instrument of claim 29 including a mechanism for locking the relative orientation between the proximal and distal movable members at a predetermined position.

34. The surgical instrument of claim 29 wherein said proximal movable member comprises a bendable member and said distal movable member comprises a pivotal joint.

35. The surgical instrument of claim 29 wherein said proximal movable member comprises a unitary slotted structure including a plurality of separately disposed non-contiguous slots.

36. An instrument comprising:
an instrument shaft having proximal and distal ends;
a proximal turnable member;
a control handle coupled to the proximal end of the instrument shaft via the proximal turnable member;
a distal turnable member
a working member coupled to the distal end of said instrument shaft via the distal turnable member;
a control element that intercouples between said proximal and distal turnable members so that a deflection of the control handle at the proximal turnable member causes a deflection of the working member via the distal turnable member
wherein at least one of the proximal and distal turnable members comprises a bendable motion member;
and a linear actuator for controlling the translation of the instrument shaft.

37. The instrument of claim 36 including an input device at the control handle to control the linear actuator.

38. The instrument of claim 36 including a force sensing element mounted on either the instrument shaft or a carriage of the linear actuator to detect the translation force.

39. The instrument of claim 36 wherein the instrument shaft is flexible for passage intraluminally.

40. The instrument of claim 36 including a distal axial rotation member.

41. A surgical instrument comprising:
an elongated instrument shaft having proximal and distal ends;
a tool disposed from the distal end of the instrument shaft;
a control handle disposed from the proximal end of the instrument shaft;
a distal bendable member for coupling the distal end of said elongated instrument shaft to said tool;
a proximal bendable member for coupling the proximal end of said elongated instrument shaft to said handle; and
actuation means extending between said distal and proximal bendable members for coupling motion of said proximal bendable member to said distal bendable member for controlling the positioning of said tool;
said proximal bendable member having a maximum transverse cross-sectional dimension that is different than that of said distal bendable member.

42. The surgical instrument of claim 41 wherein the proximal bendable member is able to axially rotate relative to the control handle.

43. The surgical instrument of claim 41 including a mechanism for locking the relative orientation between the proximal and distal bendable members.

44. The surgical instrument of claim 41 including a distal axial rotation joint for axially rotating at least one of the distal bendable member and tool relative to the instrument shaft.

45. The surgical instrument of claim 41 including a rolling-motion wheel adjacent the control handle and rotatable relative to the control handle for causing a corresponding rotation of the tool about a distal tool roll axis.

46. An instrument comprising:
an instrument shaft having proximal and distal ends;
a working member disposed from the distal end of the instrument shaft;
a control handle disposed from the proximal end of the instrument shaft;
said working member being coupled to the distal end of said instrument shaft by a distal bendable member;
said control handle coupled to the proximal end of said instrument shaft via a proximal bendable member;
whereby movement of said control handle with respect to said instrument shaft via said proximal bendable member causes attendant movement of said working member with respect to said instrument shaft via said distal bendable member;
and cables that connect said proximal and distal bendable members;

wherein said cables are disposed at a different radial distance from the center of the proximal bendable member as compared to the distal bendable member.

47. The surgical instrument of claim 46 wherein the radial distance to the cables at the proximal bendable member is greater than the radial distance to the cables at the distal bendable member.

48. The surgical instrument of claim 46 wherein the cable at each bendable member is maintained at the same radial distance along the bendable member.

49. An instrument comprising:
an instrument shaft having proximal and distal ends;
a working member disposed from the distal end of the instrument shaft;
a control handle disposed from the proximal end of the instrument shaft;
a distal bendable member for coupling the distal end of said instrument shaft to said working member;
a proximal bendable member for coupling the proximal end of said instrument shaft to said handle;
and actuating means extending between said distal and proximal bendable members for coupling motion of said proximal bendable member to said distal bendable member for controlling the positioning of said working member;
said actuating means comprising cables that are arranged so that each cable is disposed a first radial distance from the center of the distal bendable member and a second radial distance from the center of the proximal bendable member;
said first and second radial distances being different.

50. The instrument of claim 49 wherein the second radial distance is greater than the first radial distance.

51. The instrument of claim 49 further including a wheel member disposed adjacent the control handle and rotatable relative to the control handle for causing a corresponding rotation of the tool about a distal tool roll axis.

52. The instrument of claim 51 wherein both bendable members can bend in any direction, and the maximum transverse cross-sectional dimension of the proximal bendable member is different than that of the distal bendable member.

53. The instrument of claim 49 including a mechanism for locking the relative orientation between the proximal and distal bendable members at a predetermined position.

54. The instrument of claim 49 wherein said proximal bendable member comprises a unitary slotted structure including a plurality of separately disposed non-contiguous slots.

55. An instrument having a proximal control handle and a distal tool that are intercoupled by an elongated instrument shaft, proximal and distal movable members that respectively intercouple said proximal control handle and said distal tool with said instrument shaft, cabling that extends between said movable members so that a motion at said proximal movable member controls said distal movable member, and a control member at said control handle and manipulable by a user to control, via said proximal and distal movable members, the rotation of said distal tool about its distal tool axis and wherein said proximal movable member comprises a proximal bendable member.

56. The instrument of claim 55 wherein said control member comprises a rolling-motion wheel that controls the rotation about a distal tool axis that is a longitudinal axis common to both said distal movable member and said tool.

57. The instrument of claim 55 wherein said distal movable member comprises a distal bendable member.

58. The instrument of claim 55 wherein both said proximal and distal movable members each comprise a bendable member capable of bending in all directions.

59. The instrument of claim 55 wherein said control member controls the rotation of said handle about a handle longitudinal axis which, in turn, controls the rotation of said tool about a longitudinal tool axis.

60. The instrument of claim 55 wherein said control member comprises a rotation member disposed adjacent to said handle and controlled by a user to rotate the instrument shaft and proximal and distal movable members and to, in turn, cause a corresponding rotation of said tool.

61. A method of controlling a medical instrument that has a proximal end including a control handle and a distal end including a distal tool, said control handle and distal tool being intercoupled by an elongated instrument shaft that is meant to pass internally of an anatomic body, the distal tool having a longitudinal distal tool axis, said method including providing proximal and distal movable members that respectively intercouple said proximal control handle and said distal tool with said instrument shaft, extending cabling between said movable members so that a motion at said proximal movable member controls said distal movable member, manually controlling, from the proximal end of the instrument the rotation of said instrument shaft, proximal and distal movable members and distal tool about its longitudinal distal tool axis, providing a control member at the proximal end of the instrument that controls the rotation about the distal tool axis, said distal tool axis being a longitudinal axis common to both said distal movable member and said tool and wherein said movable members comprise bendable members.

62. The method of claim 61 wherein said control member controls the rotation of said proximal bendable member about a handle longitudinal axis and which, in turn, controls the rotation of said tool about the longitudinal distal tool axis.

63. The method of claim 62 wherein said control member comprises a rotation wheel disposed adjacent to said handle and controlled by a user to rotate and to, in turn, cause a corresponding rotation of said tool about the longitudinal tool axis.

* * * * *